US008492080B2

(12) United States Patent
King et al.

(10) Patent No.: US 8,492,080 B2
(45) Date of Patent: Jul. 23, 2013

(54) EMBRYO CULTURE MEDIA CONTAINING THYROID HORMONE

(75) Inventors: William Allan King, Guelph (CA); Fazl A. Ashkar, Guelph (CA)

(73) Assignee: University of Guelph, Guelph, Ontario (CA)

( * ) Notice: Subject to any disclaimer, the term of this patent is extended or adjusted under 35 U.S.C. 154(b) by 611 days.

(21) Appl. No.: 12/582,352

(22) Filed: Oct. 20, 2009

(65) Prior Publication Data

US 2010/0136512 A1 Jun. 3, 2010

Related U.S. Application Data

(60) Provisional application No. 61/106,785, filed on Oct. 20, 2008.

(30) Foreign Application Priority Data

Nov. 19, 2008 (CA) .................................. 2644091

(51) Int. Cl.
*A01N 1/00* (2006.01)

(52) U.S. Cl.
USPC ................. 435/1.3; 435/2; 435/325; 435/384

(58) Field of Classification Search
USPC .......................................................... 435/1.3
See application file for complete search history.

(56) References Cited

U.S. PATENT DOCUMENTS

| 4,987,080 A | 1/1991 | Grob et al. |
| 2007/0128727 A1 | 6/2007 | Kraemer et al. |

FOREIGN PATENT DOCUMENTS

| WO | WO88/10068 A1 | 12/1988 |
| WO | WO2007/117565 | 10/2007 |

OTHER PUBLICATIONS

Cha et al. Maturation in vitro of immature human oocytes for clinical use, Human Reproduction Update, 1998, vol. 4, p. 103-120.*
Zhang et al., Expression of multiple thyroid hormone receptor mRNAs in human oocytes, cumulus cells, and granulosa cells, Molecular Human Reproduction, vol. 3, 1997, p. 555-562.*
Abeydeera LR, Day BN. Oct. 1997. Fertilization and subsequent development in vitro of pig oocytes inseminated in a modified tris-buffered medium with frozen-thawed ejaculated spermatozoa. Biology of Reproduction, 57(4):729-34.
Fazl A. Ashkar and William Allan King, Roles(s) of Thyroid Hormones in Early Bovine Embryo Development, Nov. 21, 2007, Sixth Annual Ontario Veterinary College (OVC) Graduate Student Research Symposium, Guelph, Ontario. (Abstract and Slides for Oral Presentation).
Maruo T, Hayashi M, Matsuo H, Yamamoto T, Okada H, Mochizuki M. 1987. The role of thyroid hormone as a biological amplifier of the actions of follicle-stimulating hormone in the functional differentiation of cultured porcine granulosa cells. Endocrinology. 121(4):1233-41.
Obregon MJ, Mallow J, Pastor R, Morreale De Escobar G, Escobar Del Rey, F. L-thyroxine and 3,5,3'-triiodo-L-thyronine in rat embryos before onset of fetal thyroid function. Endocrinology. 1984. 114(1):305-307.
Sato E and Jiang JY. 2001. Follicular development and ovulation in hypothyroid rdw rats. Italian Journal of Anatomy and Embryology. 106(2 Suppl 2):249-56.
Spicer LJ, Alonso J, Chamberlain CS. 2001. Effects of thyroid hormones on bovine granulosa and thecal cell function in vitro: Dependence on insulin and gonadotropins. Journal of Dairy Science. 84(5):1069-76.
Tervit HR, Whittingham DG, Rowson LE. 1972. Successful culture in vitro of sheep and cattle ova. Journal of Reproduction and Fertility. Sep.;30(3):493-7.
F.A. Ashkar, P.m.Bartlewski, J. Singh and W.A. King, Thyroid Hormone Concentrations in Peripheral Circulation and Ovarian Follicular Fluid of Cows, 16th International Congress on Animal Reproduction (ICAR), Jul. 13-17, 2008, Budapest, Hungary. (Poster Presentation).
Antipenko, A Ye et al., "Thyroid hormones and regulation of cell reliability systems. Advances in enzyme regulation", 1994, vol. 34, p. 173-198.
Du Plessis, SS et al., "Impact of oxidative stress of IVF", Expert Review of Obstretrics and Gynecology, Jul. 2008, vol. 3, p. 539-554.

* cited by examiner

*Primary Examiner* — Jon P Weber
*Assistant Examiner* — Tiffany Gough
(74) *Attorney, Agent, or Firm* — Bereskin & Parr LLP/S.E.N.C.R.L., s.r.l.; Micheline Gravelle

(57) ABSTRACT

The disclosure relates to the use of culture media containing thyroid hormones or analogs thereof, and includes methods and uses thereof for embryo culture, embryo production, embryo maturation, improved survival of embryos and improved viability of embryos post cryopreservation.

18 Claims, 27 Drawing Sheets

1

EMBRYO CULTURE MEDIA CONTAINING THYROID HORMONE

This application claims the benefit of U.S. provisional application Ser. No. 61/106,785, filed Oct. 20, 2008 and Canadian Patent Application No. 2,644,091, filed Nov. 19, 2008, both of which are incorporated herein by reference in their entirety.

FIELD OF THE DISCLOSURE

The present disclosure relates to a culture media comprising thyroid hormone for use during in vitro embryo production. The media is useful for culturing, producing, and maturing embryos, improving the survival and viability of embryos following in vitro fertilization and improving the survival and viability of embryos after cryopreservation.

BACKGROUND OF THE DISCLOSURE

Early embryo development, defined as the period starting with oocyte maturation and fertilization and ending with blastocyst formation also known as pre-implantation, is a period in which many embryos die or cease development. This appears to be significantly higher when embryos are produced by in vitro fertilization or cloning (in animals) and/or after cryopreservation. Several important events in early embryo development include oocyte maturation and sperm capacitation, fertilization, cleavage, compaction, and blastocyst formation. In the in vivo condition these events occur in the female reproductive tract, which provides an optimal environment for embryo development.

With the advent of Assisted Reproductive Technology a revolution happened in reproduction biology and biotechnology, which resulted in the production "test tube" embryos in different species. With respect to humans, infertility treatment is widely implemented given the abundance of advanced reproductive technologies available. Currently, the success rate of flushing a woman for multiple oocytes, followed by in vitro fertilization, embryo transfer and pregnancy is quiet low (<25%). Most women have to go through multiple cycles of hormone stimulation to obtain multiple embryos. Hormone stimulation is a significant risk with possible severe negative effects. Consequently, any aspect of in vitro embryo production (IVP) that can increase the resiliency and success of embryo survival will reduce the number of embryos needed to be collected and the number of times a woman is super ovulated in order to obtain oocytes to produce embryos by in vitro fertilization (IVF) for embryo transfer.

Further, with the development of cryopreservation, eggs and/or fertilized eggs (embryos) may be stored for future use, such as embryo transfer. With respect to humans, this may allow women to store young normally ovulated eggs and/or fertilized eggs (embryos) obtained during the prime reproductive years, and use them when they are older. Current methods of cryopreservation remain problematic since frozen-thawed embryos lack viability and are prone to apoptosis, which limits their utility in embryo transfer. Thus, any aspect of cryopreservation that improves the survival of eggs or embryos post cryopreservation is tremendously beneficial.

One of the most important parts of in vitro embryo production is culture media and its composition for the various stages of early embryo development. For the past four decades researchers in this field have attempted to optimize the usefulness of in vitro media, including media for in vitro maturation (IVM) of oocytes, media for in vitro fertilization (IVF) of oocytes with sperm, and media for in vitro culture (IVC) of embryos. However in vitro embryo development and survival remains problematic. Each period in early embryo development represents different stages which have distinct growth factor requirements. In vivo, there are tremendous autocrine, paracrine and endocrine factors which are integrated and act during the different stages of early embryo development.

An example of these factors are the thyroid hormones, produced and secreted by the thyroid gland in response to stimulation by thyroid stimulating hormone (TSH), which is released by the pituitary gland. In vivo, thyroid hormones are mainly expressed in two forms, thyroxine (T4) and triiodothyronine (T3) and at a serum concentration ratio of approximately 20:1, respectively. In blood, most of this thyroid hormone is bound to carrier protein molecules (thyroxine-binding globulin, transthyretin, or albumin). In blood, unbound hormone is called free thyroid hormone which is biologically more active than bound thyroid hormone. Free T3 (fT3) is three to four times more potent than free T4 (fT4) and is created as needed within tissues using deiodinases (5'-iodinase) to convert T4 to T3. Thyroid hormones play an important role in vertebrate growth, differentiation and metabolism.

For example, one study indicated that infertile immature spontaneously hypothyroid RDW female rats had significantly more ovulated eggs and improved follicular development following treatment with T4 and equine chorionic gonadotropin (eCG) (Sato E et al. 2001). Treatment of bovine granulosa cells with T3 and T4 caused an increase in net estrogen production (L. J Spicer 2001). T3 synergizes with follicle-stimulating hormone (FSH) to induce differentiation of granulosa cells in porcine follicles (Maruo et al. 1987).

The use of thyroid hormone for initial stages of in vitro oocyte maturation is disclosed in U.S. Pat. No. 4,987,080 (issued in 1991). Specifically, this patent discloses incubation of oocytes in culture media containing one or more thyroid hormones for the growth and development of small and medium oocytes into large oocytes. However, this patent suggests and discloses the use of a different culture media that does not include thyroid hormones for subsequent stages of development, including ova maturation, in vitro fertilization, early cleavage of the embryo, and growth of the embryo to the blastocyst stage. The culture media disclosed for use in these steps is described as having low nutrients and a high energy source, and may include bovine serum albumin.

SUMMARY OF THE DISCLOSURE

The present inventors have investigated the role of thyroid hormones during early embryo development and have demonstrated that the use of in vitro culture media containing thyroid hormone for in vitro production of embryos has a beneficial effect on embryo development, maturation, production, viability and survival of embryos. The inventors further demonstrated improved viability and survival of thawed embryos post cryopreservation using culture media containing thyroid hormone.

The present disclosure describes the detection and quantification of the concentration of thyroid hormones in bovine serum and ovarian follicular fluid. The present disclosure also describes the expression of thyroid hormone receptors detected in harvested untreated bovine germinal vesicles (immature oocytes), in vitro mature oocytes and eight day old embryos (blastocysts) cultured in media containing thyroid hormone, and in vivo in harvested eight day old embryos. This data provides support for the therapeutic effects of culture media comprising thyroid hormone disclosed in the present disclosure for use during in vitro embryo production including producing and maturing embryos, improving survival of embryos, and improving the viability of embryos post cryopreservation.

Therefore a culture media comprising thyroid hormone or analog thereof is useful for in vitro embryo production, including culturing embryos, producing embryos, maturing embryos, improving the survival of embryos, and improving the viability of embryos post cryopreservation.

Accordingly, the present disclosure includes an in vitro culture media (IVCM) for in vitro embryo production and includes an in vitro culture media comprising a thyroid hormone or analog thereof (IVCMT) for in vitro embryo production. The present disclosure also includes the use of an in vitro culture media comprising a thyroid hormone or analog thereof (IVCMT) for in vitro embryo production.

In one embodiment, the thyroid hormone is triiodothyronine (T3). In another embodiment, the thyroid hormone is thyroxine (T4). In another embodiment, the thyroid hormone is a combination of triiodothyronine and thyroxine (T3/T4). In another embodiment, the analog comprises functional fragments of thyroid hormone or peptide mimetics.

Another aspect of the present disclosure is the use of IVCMT for in vitro embryo production wherein in vitro embryo production comprises use of the IVCMT for: culturing embryos; producing embryos; maturing embryos; improving survival of embryos; and improving viability of embryos post cryopreservation.

One aspect of the present disclosure is a method of in vitro embryo production comprising culturing fertilized oocytes in IVCMT. Another aspect of the present disclosure is a method of in vitro embryo production wherein in vitro embryo production comprises a method of producing embryos, the method comprising culturing fertilized oocytes in IVCMT until the embryos are produced.

Another aspect of the present disclosure is a method of in vitro embryo production wherein in vitro embryo production comprises a method of maturing embryos, the method comprising culturing fertilized oocytes in IVCMT until the embryos are matured.

A further aspect of the present disclosure is a method of in vitro embryo production where in vitro embryo production comprises a method of improving survival of embryos, the method comprising culturing fertilized oocytes in IVCMT. In one embodiment, the embryos cultured in the IVCMT exhibit improved survival as compared to embryos that were not cultured in IVCMT.

Another aspect of the present disclosure is a method of in vitro embryo production where in vitro embryo production comprises a method of improving viability of embryos post cryopreservation, the method comprising (a) culturing fertilized oocytes in IVCMT until embryos are produced; and (b) freezing and storing the embryos in cryopreservation media to create cryopreserved embryos. In one embodiment, the embryos cultured in the IVCMT exhibit improved viability post cryopreservation as compared to embryos that were not cultured in the IVCMT prior to cryopreservation.

Other features and advantages of the present disclosure will become apparent from the following detailed description. It should be understood, however, that the detailed description and the specific examples while indicating preferred embodiments of the present disclosure are given by way of illustration only, since various changes and modifications within the spirit and scope of the present disclosure will become apparent to those skilled in the art from this detailed description.

BRIEF DESCRIPTION OF THE DRAWINGS

The disclosure will now be described in relation to the drawings in which.

DETAILED DESCRIPTION OF THE DISCLOSURE

Figure 1A:
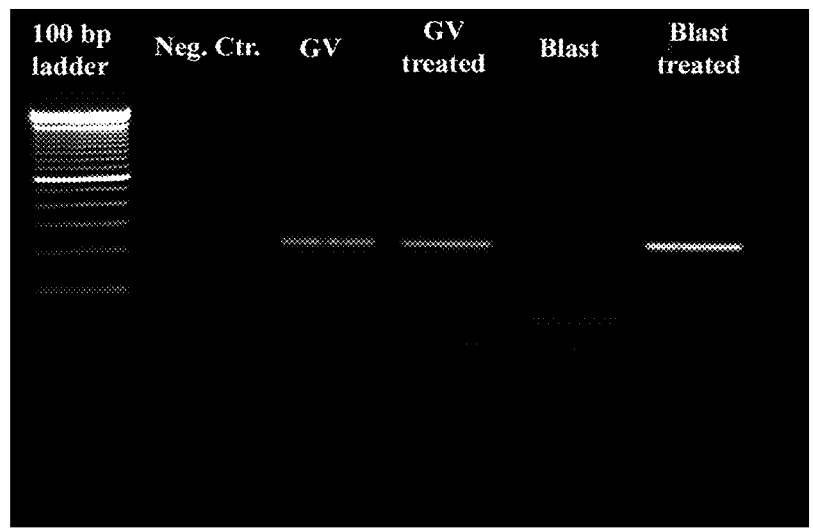
FIG. 1A is a 1DE-agarose gel demonstrating the positive identification of thyroid receptor gene expression (DNA) detected via RT-PCR in untreated in vivo immature bovine oocytes (GV), T3/T4 treated mature oocytes (GV treated), and T3/T4 treated blastocysts (Blast treated) but not in control blastocysts (Blast).
Figure 1B:
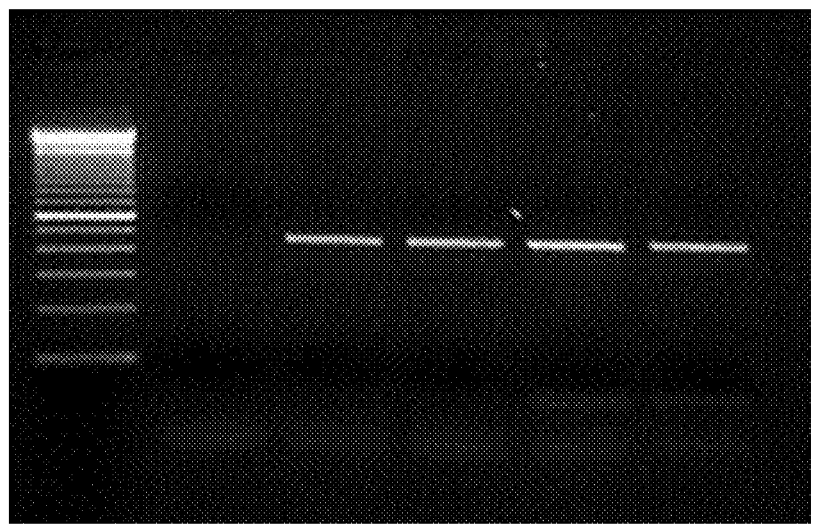
FIG. 1B is a 1DE-agarose gel demonstrating the identification of Beta Actin as a positive control for the RT-PCR process.
Figure 1C:
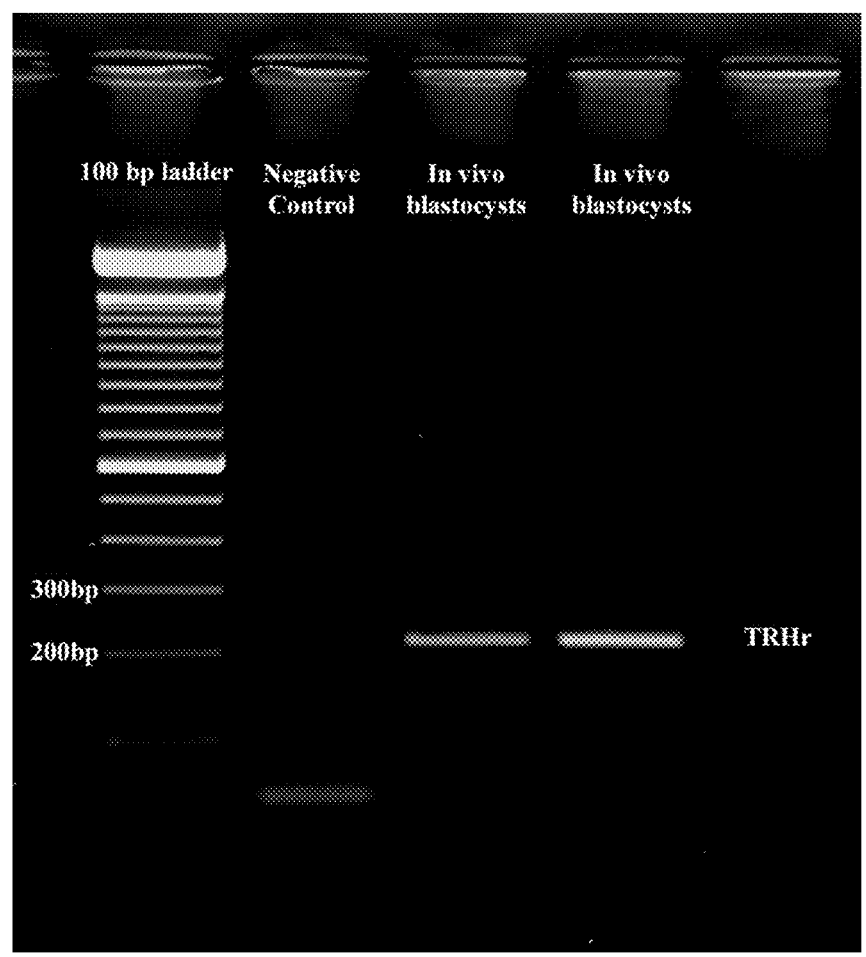
FIG. 1C is a 1DE-agarose gel demonstrating the positive identification of thyroid receptor gene expression (DNA) detected via RT-PCR in two repeated trials of untreated in vivo bovine embryos (in vivo blastocysts).
Figure 2A:
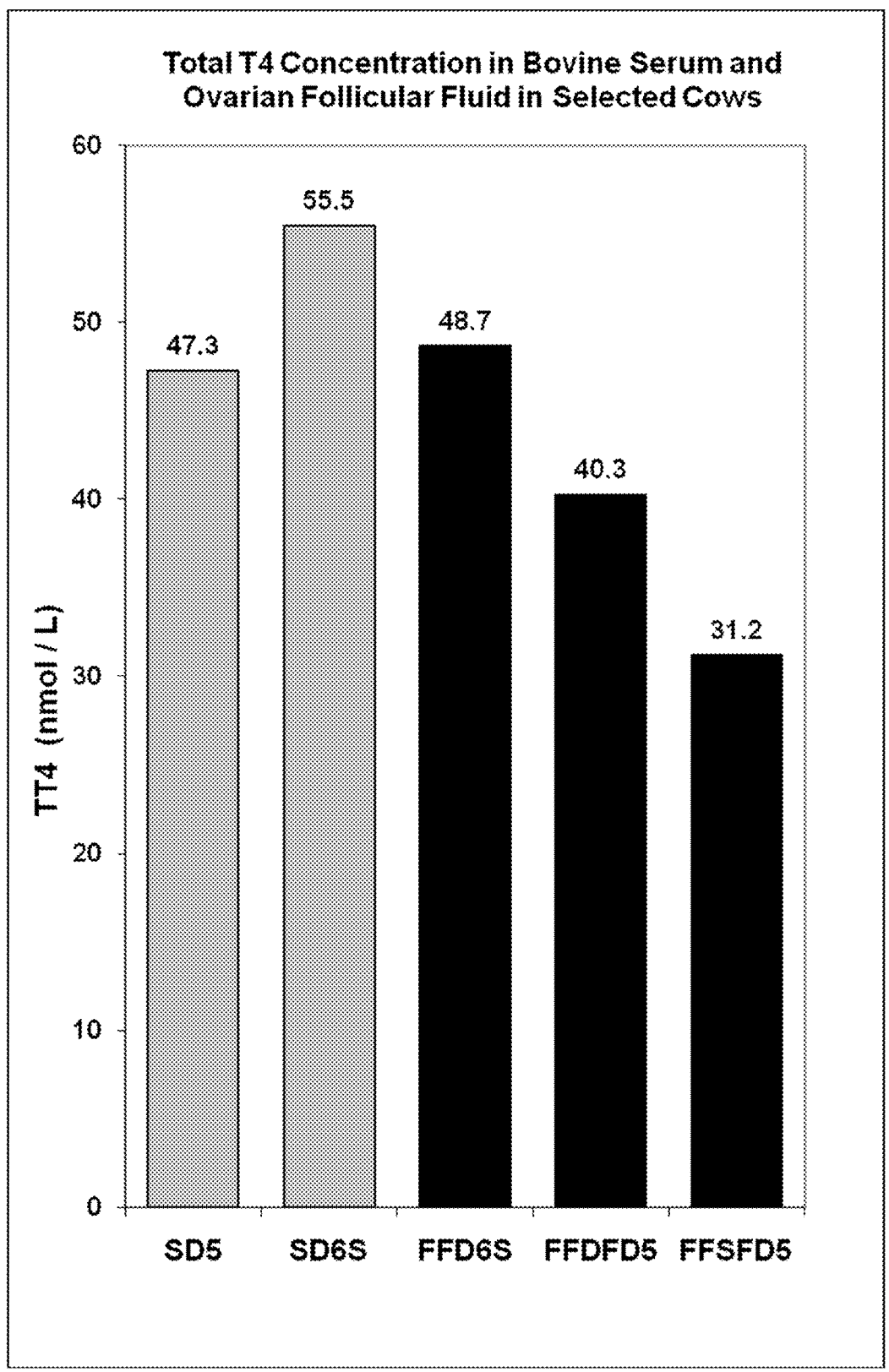
FIG. 2A is a graph showing total T4 hormone concentration in bovine serum and ovarian follicular fluid, in selected cows (n=15).
Figure 2B:
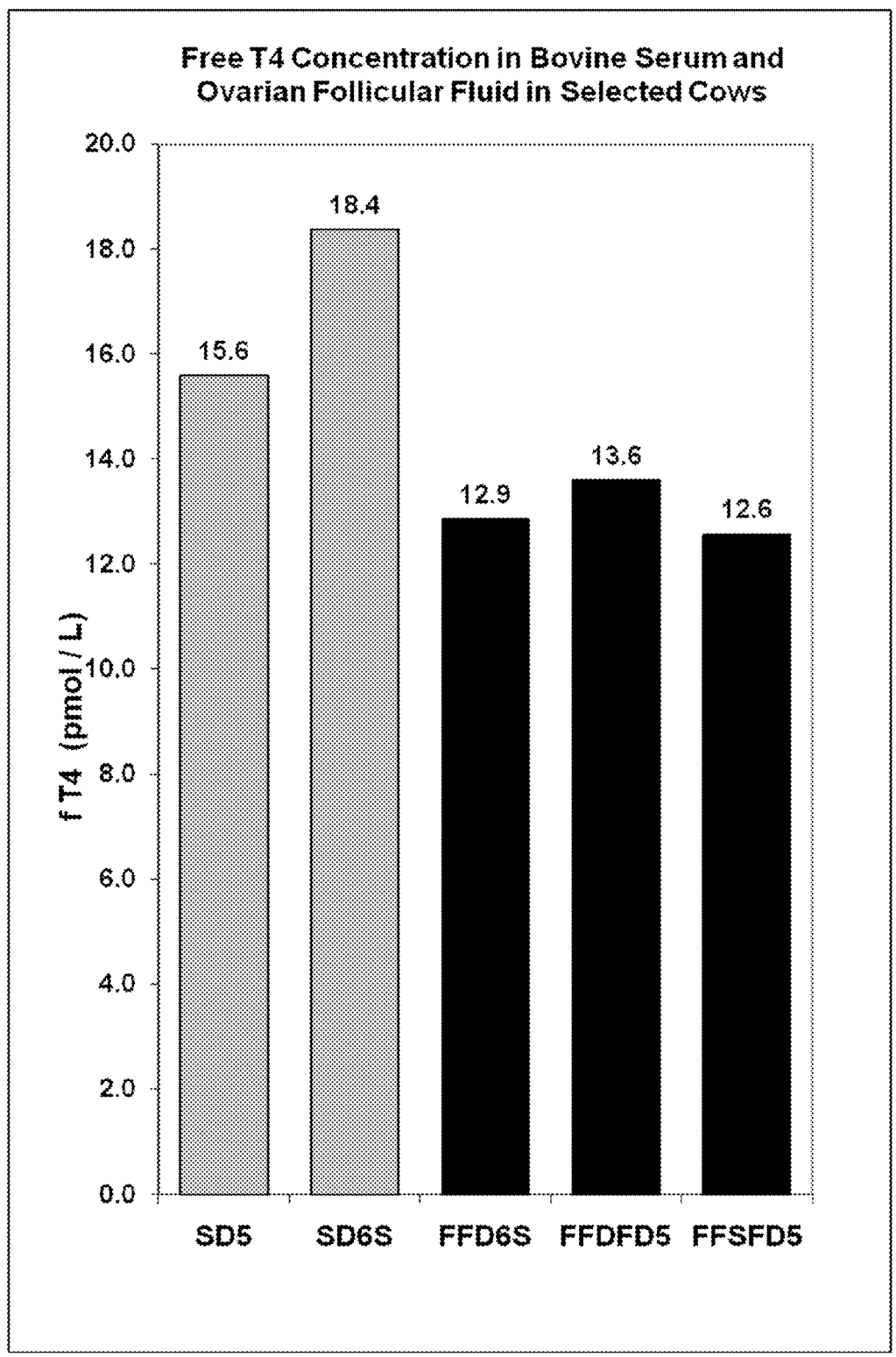
FIG. 2B is a graph showing free T4 hormone concentration in bovine serum and ovarian follicular fluid, in selected cows (n=15).
Figure 3A:
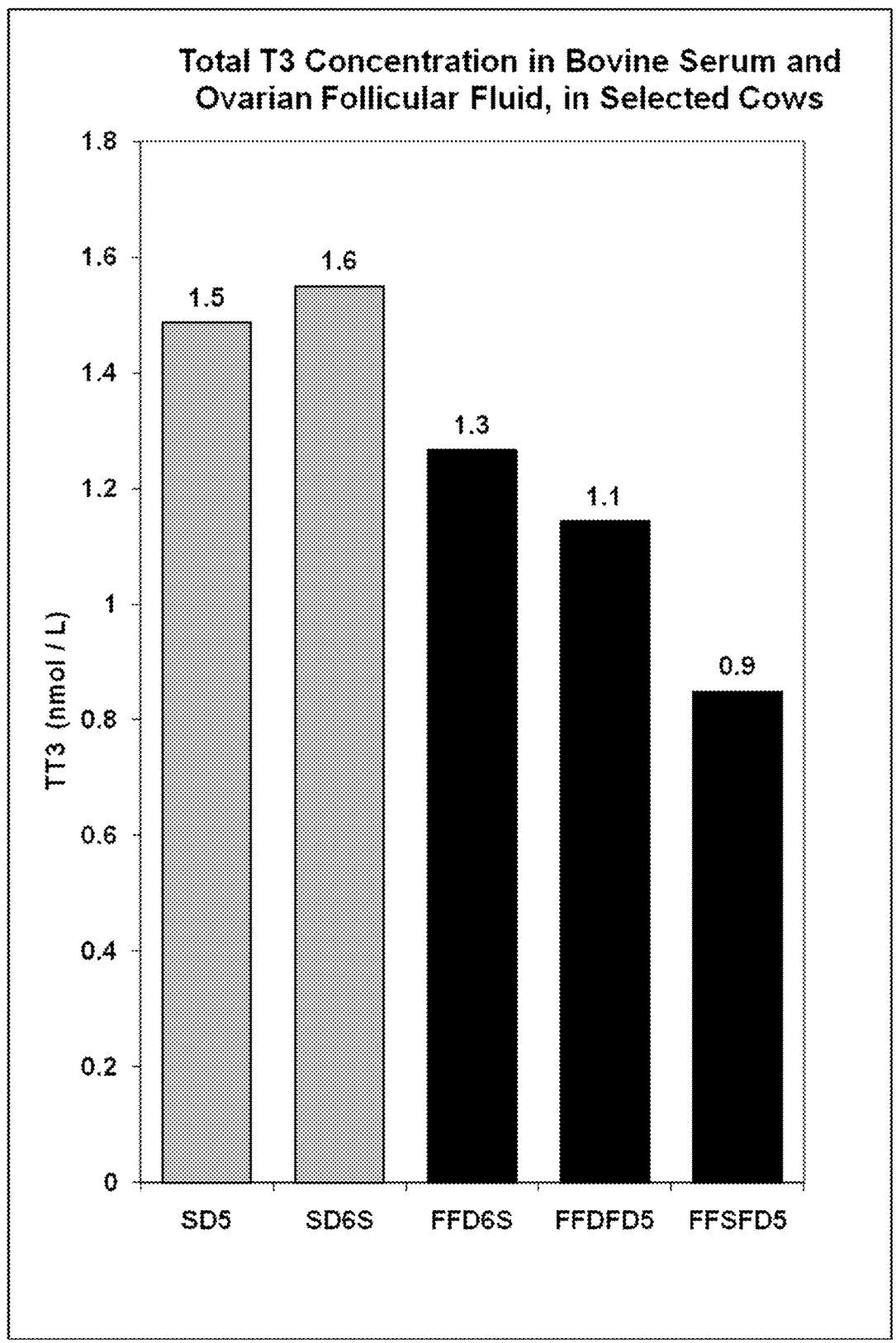
FIG. 3A is a graph showing total T3 hormone concentration in bovine serum and ovarian follicular fluid, in selected cows (n=15).
Figure 3B:
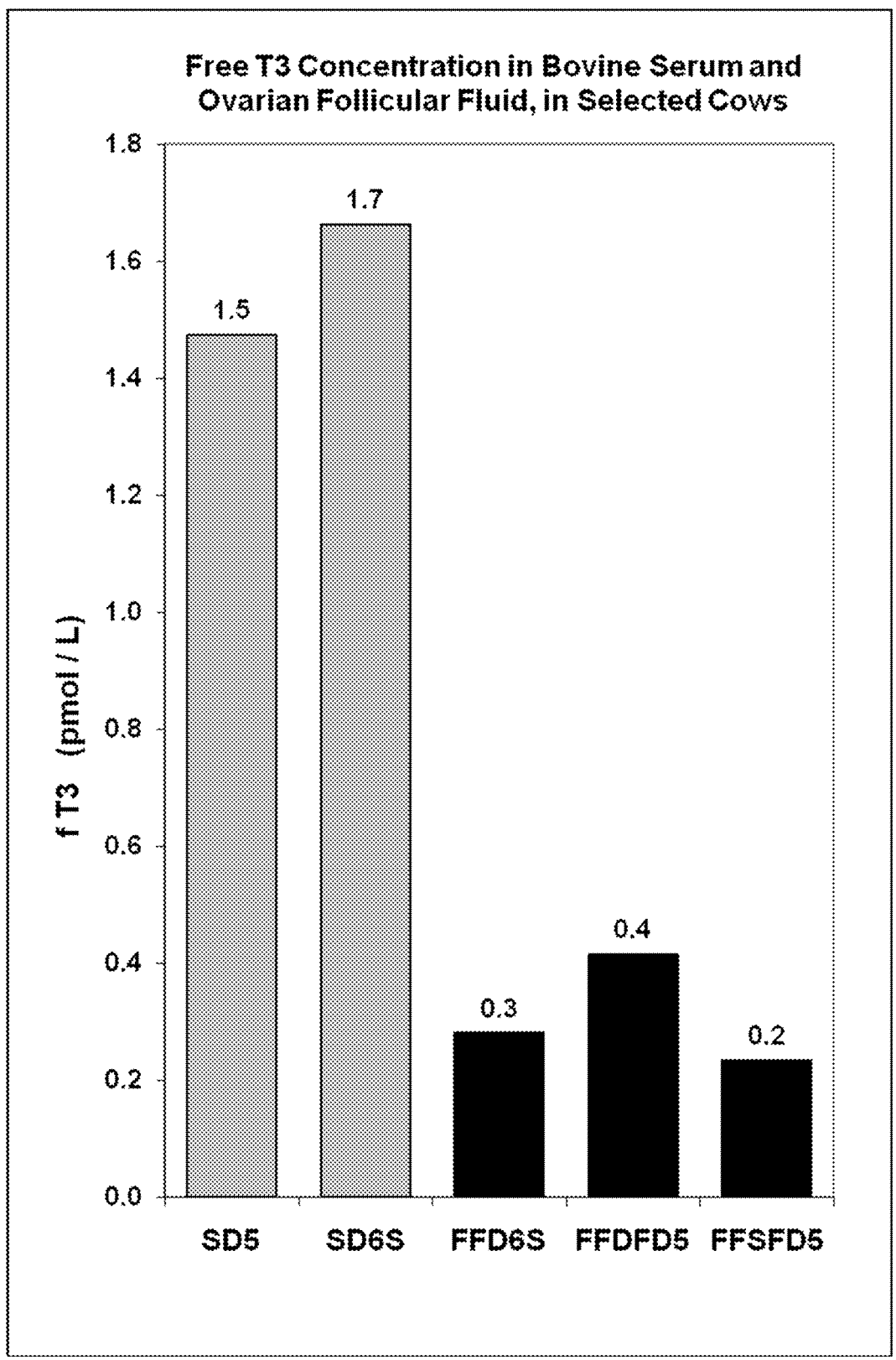
FIG. 3B is a graph showing free T3 hormone concentration in bovine serum and ovarian follicular fluid, in selected cows (n=15).

As described above, the present disclosure provides data that quantified the concentration of thyroid hormones in bovine serum and ovarian follicular fluid in selected cows (n=15) (FIGS. 2 and 3), which provided an estimate of the physiological levels to which oocytes and embryos are exposed in the reproductive tract. The present disclosure also describes expression of thyroid hormone receptors detected in bovine germinal vesicles (immature oocytes), mature oocytes and eight day old embryos (blastocysts) cultured in IVCMT, and in blastocysts produced in vivo (ie collected from the reproductive tracts of cows 7 days after insemination), using reverse transcriptase polymerase chain reaction (RT-PCR) and one dimensional electrophoresis (1 DE) (FIGS. 1A, 1B, 1C).

Accordingly, and as mentioned above, the present disclosure includes an in vitro culture media (IVCM) comprising a thyroid hormone or analog thereof (IVCMT) for use in in vitro embryo production. The present disclosure identified a beneficial effect of the use of IVCMT disclosed herein, on in vitro embryo production, including embryo development, production, maturation and improved viability and survival of bovine embryos as demonstrated in FIGS. 5-8 and porcine embryos in FIGS. 15-16. The present disclosure also identified a cryoprotective effect, including improved hatching, viability and survival of frozen-thawed bovine embryos treated with IVCMT as shown in FIGS. 9 and 10 and Table 1. The present disclosure also determined that the beneficial effect of the IVCMT media occurs during the IVC stage (FIG. 12), and not during IVM (FIG. 11).

As described more fully below, the IVCMT may be used for in vitro embryo production, which includes for example embryo culture, embryo production, embryo maturation, improving survival of embryos, and improving viability of embryos post cryopreservation.

Accordingly, the present disclosure includes an in vitro culture media comprising a thyroid hormone or analog thereof (IVCMT). The present disclosure includes an in vitro culture media comprising a thyroid hormone or analog thereof (IVCMT) for in vitro embryo production. The present disclosure also includes use of a culture media (IVCM) comprising a thyroid hormone or analog thereof (IVCMT) for in vitro embryo production.

The term "IVCM" as used herein means any in vitro culture media known in the art used to culture, mature and produce embryos beginning at the zygote stage to the blastocyst stage (or pre-implantation stage) of embryonic development. The term "IVCMT" as used herein describes IVCM comprising a thyroid hormone or analog thereof.

As used herein the term "in vitro embryo production" includes embryo culture or culturing embryos, embryo production or producing embryos, embryo maturation or maturing embryos, improving survival of embryos, and improving viability of embryos post cryopreservation.

The term "embryo" or "embryos" as used herein describes mammals at the earliest stages of embryonic development following oocyte fertilization and includes embryos from the zygote stage, to morula, to the blastocyst stage of embryonic development. The blastocyst stage of embryonic development, which is characterized by the formation of a blastocoele, is reached approximately 6 days after fertilization. At this stage, blastocysts begin hatching from their outer shell, known as the zona pellucida. Blastocyst stage also describes embryonic developmental stages that include, for example, very early blastocysts, early blastocysts, expanded blastocysts, hatching blastocysts and hatched blastocysts. Blastocysts are also known as pre-implantation embryos, and thus may be transferred (embryo transfer) to a uterus for implantation or may be stored via cryopreservation for later use.

The term "mammals" as used herein includes all members of the class mammalia such as bovine, porcine, equine, ovine, canine, and preferably, human mammals.

The term "thyroid hormone" means a tyrosine-based hormone secreted by the thyroid gland in response to stimulation by thyroid stimulating hormone (TSH), which is produced by the pituitary gland. TSH is released in response to stimulation by thyrotrophin releasing hormone (TRH), which is produced in the hypothalamus. Thyroxine (T4) also known as 3,5,3',5'-tetra-iodothyronine is the major thyroid hormone in blood. Triiodothyronine (T3) also know as 3,3',5-triiodo-L-thyronine is a more active form of thyroid hormone and is formed by converting T4 using cellular deiodinases. Most thyroid hormone circulating in the blood is bound to transport proteins, and only a small fraction is unbound. When thyroid hormones are measured in blood and serum, the unbound fractions are called freeT3 (fT3) and free T4 (fT4) to differentiate them from total T3 (TT3) and total T4 (TT4), respectively, which contain both bound and unbound fractions. Unbound thyroid hormones (fT3 and fT4) are more biologically active, thus circulating levels of free T3/T4 are important for many biological processes. Other forms of thyroid hormones like reverse T3 (rT3) or diiodothrozine (T2) are produced in tissues due to deiodonization of T4 and T3 and each can have different biological effects. Although thyroid hormones have their own receptors, they can also act through the steroid super-family of receptors.

The term "thyroid hormone" described above also includes synthetic versions of endogenous or physiological forms of thyroid hormone described herein. The term "synthetic" in reference to thyroid hormone means a chemically synthesized form of endogenous or physiological thyroid hormone. For example, levothyroxine, also known as synthetic T4, L-thyroxine, or 3,5,3',5'-tetraiodo-L-thyronine, is a synthetic chemically manufactured stereoisomer of physiological thyroxine. Levothyroxine is metabolized more slowly than physiological thyroxine and it is the most common synthetic T4 used in humans. Synthetic forms of T3 and/or T4 may be obtained commercially. Another example of commercial synthetic T4 is T2501 L-Thyroxine sodium salt pentahydrate (Sigma-Aldrich, Oakville, ON). An example of commercially available synthetic T3 is T6397 3,3',5-Triiodo-L-thyronine sodium salt powder (Sigma-Aldrich, Oakville, ON).

The term "analog thereof" in reference to a thyroid hormone includes any agent that functions as a thyroid hormone such as for example T3 and/or T4. The term may include functional or active fragments of thyroid hormone that are capable of binding to the thyroid receptor and inducing a response. Alternatively, "analog thereof" may be any active agent that is capable of binding to the thyroid receptor and inducing a response, and may include peptide mimetics and the like. As used herein the term "active" refers to molecules in proper conformation, which are thus capable of binding to the thyroid receptor. As used herein, the term "inducing a response" refers to molecules that increase the function or activity of thyroid hormone when compared to otherwise same conditions. Peptide mimetics include synthetic structures that may serve as substitutes for peptides in interactions between molecules (see Morgan and Gainor. (1989), Ann. Reports Med. Chem. 24:243-252 for a review). Peptide mimetics may be designed to retain structural and functional features and thus may be suitable substitutes of the thyroid hormone analog described in the present disclosure.

In one embodiment, the thyroid hormone in the IVCMT is T3. In another embodiment, the thyroid hormone in the IVCMT is T4. In another embodiment, the thyroid hormone in the IVCMT is a combination of T3 and T4. In another embodiment, the thyroid hormone added is synthetic. In another embodiment, the thyroid hormone is obtained commercially. In another embodiment, the thyroid hormone is synthetic and obtained commercially. In another embodiment, the synthetic T4 added is T2501, L-Thyroxine sodium salt pentahydrate (Sigma-Aldrich). In another embodiment, the synthetic T3 added is T6397 3,3',5-Triiodo-L-thyronine sodium salt powder (Sigma-Aldrich). In another embodiment, the analog in the IVCMT comprises functional fragments of thyroid hormone or peptide mimetics.

In one embodiment, the thyroid hormone or analog thereof in the IVCMT may be added at a concentration in the range of from about 0.1 pmol/L to about 100 ng/ml. In another embodiment, the thyroid hormone or analog thereof is added at a concentration of about 50 ng/ml. The concentration may be adjusted to provide the optimal therapeutic effect. The inventors have determined the concentration of thyroid hormone in bovine serum and follicular fluid as demonstrated in FIGS. 2 and 3.

The IVCM culture media described herein may additionally comprise other agents useful for culturing embryos. In one embodiment, the IVCM described herein comprises a mixture of components. In one aspect, IVCM comprises oviduct fluid as a component. In another aspect, the IVCM comprises synthetic oviduct fluid as a component. In another aspect, the IVCM further comprises sodium pyruvate as a component. In another aspect, the IVCM comprises non essential amino acids as a component. In another aspect, the IVCM further comprises essential amino acids as a component. In a further aspect, the IVCM also comprises about EFAF BSA 14-17% in SOF, including about EFAF BSA 15% in SOF as a component. In another aspect, the IVCM comprises bovine steer serum as a component. In one embodiment, the IVCM comprises one or more of the following components: oviduct fluid or synthetic oviduct fluid, sodium pyruvate, non essential amino acids, essential amino acids, about EFAF BSA 15% in SOF, and bovine steer serum. In a specific embodiment, IVCM comprises: approximately 8-12 ml synthetic oviduct fluid (SOF), including about 10 ml SOF (BSS0460, Chemicon-Millipore, Billerica, Mass.); approximately 45-55 ul sodium pyruvate, including about 50 ul sodium pyruvate (P4562-5G, Invitrogen, Burlington, ON); approximately 180-220 ul non essential amino acids 100×, including about 200 ul non essential amino acids 100× (11140050, Invitrogen); approximately 90-110 ul essential amino acids, including about 100 ul essential amino acids (11130051, Invitrogen); approximately 4-6 ul gentamicin, including about 5 ul gentamicin (G-1397, Invitrogen); approximately 500-615 ul EFAF BSA 15% in SOF, including about 560 ul EFAF BSA 15% in SOF (A-88096-5G, Sigma-Aldrich, Oakville, ON); and approximately 180-220 ul bovine steer serum, including about 200 ul bovine steer serum (B15008, PAA Lab formerly Cansera, Rexdale, ON).

In another aspect, the IVCM may be obtained as a commercially available embryo culture media. In one aspect, the IVCM commercially available media may be M7167 M2 medium (Sigma-Aldrich). In another aspect, the IVCM commercially available media may be Global medium (LifeGlobal). In a further aspect, the IVCM commercially available media may be G-2™ v5 PLUS medium (Vitrolife). In another embodiment, T3 and/or T4 may be added to the commercially available embryo culture media.

In a specific embodiment, IVCMT comprises IVCM with about 50 ng/ml T4 (T2501, L-Thyroxine sodium salt pentahydrate, Sigma-Aldrich) and about 50 ng/ml T3 (T6397 3,3',5-Triiodo-L-thyronine sodium salt powder, cell culture tested, Sigma-Aldrich).

In one aspect, the IVCMT disclosed herein may be used for in vitro embryo production. In another aspect, use of the IVCMT for in vitro embryo production comprises use of the IVCMT for culturing embryos. In one embodiment, the embryos include mammalian embryos, such as for example, bovine, porcine and particularly human embryos. In another aspect, the IVCMT disclosed herein may be used to optimize the in vitro embryo production environment resulting in enhanced embryo transfer and live birth success in mammals, including bovine, porcine and preferably, human.

The term "culturing embryos" or "embryo culture" means the process of growing embryos in vitro during in vitro culture (IVC), following in vitro fertilization (IVF).

In another aspect, the present disclosure includes a method of in vitro embryo production comprising culturing fertilized oocytes in IVCMT. Another aspect of the present disclosure is a method of in vitro embryo production wherein in vitro production comprises a method of producing embryos, the method comprising culturing fertilized oocytes in IVCMT until the embryos are produced. The disclosure also includes the use of the IVCMT described herein for in vitro embryo production, wherein in vitro embryo production comprises use of the IVCMT for producing embryos in culture. In another aspect, the method of producing embryos comprising culturing fertilized oocytes with IVCMT or the use of IVCMT for producing embryos minimizes the number of embryos required for embryo transfer in mammals, including bovine, porcine and preferably human mammals.

The phrase "producing embryos" or "embryo production" means the process following in vitro fertilization of producing embryos in vitro during in vitro culture (IVC).

As used herein, the phrase "fertilized oocytes" refers to the oocytes that are the result of in vitro fertilization.

As used herein, the terms "embryo transfer" or "transferring an embryo" describe the process of transferring an embryo into a uterus for implantation in the uterine wall.

Another aspect of the present disclosure is a method of in vitro embryo production wherein in vitro embryo production comprises a method of maturing embryos, the method comprising culturing fertilized oocytes in IVCMT until the embryos are matured. The disclosure also includes the use of the IVCMT described herein for in vitro embryo production, wherein in vitro embryo production comprises the use of the IVCMT described herein for maturing embryos in culture.

In another aspect, the method of maturing embryos comprising culturing fertilized oocytes with IVCMT or the use of IVCMT for maturing embryos disclosed herein results in matured embryos that survive embryo transfer and implantation. In another aspect, the method of maturing embryos comprising culturing fertilized oocytes with IVCMT or the use of IVCMT for maturing embryos disclosed herein results in matured embryos that exhibit an increased rate of development and increased rate of cell division over a given period of time.

In another aspect, the method of maturing embryos comprising culturing fertilized oocytes with IVCMT or the use of IVCMT for maturing embryos disclosed herein minimizes the number of embryos required for embryo transfer in mammals, including bovine, porcine and preferably human mammals.

The phrase "maturing embryos" or "embryo maturation" as used herein means events following in vitro fertilization that are indicative of embryonic development. Embryonic development and maturation after fertilization includes increase in cell numbers, compaction (morulae stage) hatching of the embryo, blastocoel formation, blastocyst stage, blastocyst expansion and finally hatching of embryos. Thus events indicative of embryonic maturation include the rate of hatching, rate of blastocyst formation, and the total cell number per blastocyst. Thyroid hormones may participate in embryo maturation through different pathways, including translational, transcriptional and post-transcriptional mechanisms and mitochondrial activation in the various stages of early embryo development.

A further aspect of the present disclosure is a method of in vitro embryo production comprising a method of improving survival of embryos, the method comprising culturing fertilized oocytes in IVCMT. In one embodiment, the embryos cultured in the IVCMT exhibit improved survival as compared to embryos that were not cultured in the IVCMT. The disclosure also includes the use of IVCMT for in vitro embryo production wherein in vitro embryo production comprises the use of the IVCMT for improving the survival of embryos. In one embodiment, the use of the culture media results in an improvement in survival of embryos as compared to embryos wherein the IVCMT is not used.

In another aspect, the method of improving the survival of embryos comprising culturing fertilized oocytes with IVCMT or the use of IVCMT for improving survival of embryos disclosed herein minimizes the number of embryos required for embryo transfer in mammals, including bovine, porcine and preferably humans. In another aspect, the method of improving the survival of embryos comprising culturing fertilized oocytes with IVCMT or the use of IVCMT for improving survival of embryos disclosed herein results in adequate embryos for embryo transfer, thus reducing the number of embryos needed to be collected and therefore the number of times a mammal is super-ovulated. In another aspect, the mammal includes bovine, porcine and preferably, human.

The phrase "improving survival of embryos" means an increase in the yield and viability of embryos during IVC following IVF as compared to and embryos that were not cultured in IVCMT. Improved survival of a population of embryos may be assessed by measuring the rate of embryos hatching out from the zona pellucida, the total number of blastocysts formed, and the number of apoptotic cells present per blastocyst.

Another aspect of the present disclosure is a method of in vitro embryo production comprising a method of improving viability of embryos post cryopreservation, the method comprising (a) culturing fertilized oocytes in IVCMT until embryos are produced; and (b) freezing and storing the embryos in cryopreservation media to create cryopreserved embryos. In one embodiment, the embryos cultured in the IVCMT exhibit improved viability post cryopreservation as compared to embryos that were not cultured in the IVCMT. The disclosure also includes the use of the IVCMT for in vitro embryo production comprising use of the IVCMT for improving viability of embryos post cryopreservation. In one embodiment, the use of the IVCMT results in improved viability of the embryos post cryopreservation as compared to embryos wherein the IVCMT is not used.

In another aspect of the present disclosure, the method of improving the viability of embryos post cryopreservation comprising culturing fertilized oocytes with IVCMT or the use of IVCMT for improving the viability of embryos post cryopreservation disclosed herein may be used to improve embryo viability after any type of cryopreservation, which may improve the overall rate of live birth success from embryo transfer. In a further aspect, the method of improving the viability of embryos post cryopreservation comprising culturing fertilized oocytes with IVCMT or the use of IVCMT for improving the viability of embryos post cryopreservation disclosed herein may be used to improve embryo viability after any type of cryopreservation, thus reducing the number of embryos needed to be collected and therefore the number of times a mammal including bovine, porcine and preferably, human is super-ovulated.

In one aspect, the method of improving the viability of embryos post cryopreservation comprising culturing fertilized oocytes with IVCMT or the use of IVCMT for improving the viability of embryos post cryopreservation disclosed herein may be used to improve embryo viability post cryopreservation, resulting in embryos adequate for embryo transfer, thus improving the overall rate of live birth success from embryo transfer in a mammal including bovine, porcine and preferably, human. In another aspect, the method of improving the viability of embryos post cryopreservation comprising culturing fertilized oocytes with IVCMT or the use of IVCMT for improving the viability of embryos post cryopreservation disclosed herein minimizes the number of embryos for embryo transfer in mammals, including bovine, porcine and preferably human mammals. In another aspect, the method of improving the viability of embryos post cryopreservation comprising culturing fertilized oocytes with IVCMT or the use of IVCMT for improving the viability of embryos post cryopreservation disclosed herein reduces the number of embryos needed to be collected and therefore the number of times a mammal including bovine, porcine and preferably, human is super-ovulated.

The phrase "improving viability of embryos post cryopreservation" means an increase in the health, yield and utility of embryos that were cryopreserved as compared to embryos that were not cultured in IVCMT. Improved viability of embryos post cryopreservation may be demonstrated by measuring the number (i.e. yield) of embryos hatching, the number of surviving blastocysts, and/or the number of apoptotic cells in an embryo. While not wishing to be bound by a particular theory, improved embryo viability may be linked to the action of thyroid hormone on the mitochondria or gene expression of the embryo.

As used herein the terms "cryopreserving" and "cryopreservation" mean the process of preserving tissue by cooling or freezing the tissue. In one aspect, the tissue is preserved or frozen in liquid nitrogen. In another aspect, the tissue is preserved or frozen in liquid nitrogen at a temperature of approximately −196° C. The term "cryopreservation media" includes media used for the process of cryopreservation. Cryopreservation media may or may not include thyroid hormone or an analog thereof. The term "cryopreserved embryos" includes embryos subjected to the process of cryopreservation.

In one aspect, the culturing step in the methods described above may occur for a period of 5-8 days. In another aspect, culturing may occur for a period of 5 days. In another aspect, the culturing step may be determined by a person skilled in the art depending on the species.

In another aspect, the methods described above may further include the additional steps of in vitro oocyte retrieval, oocyte maturation, and in vitro fertilization prior to culturing the fertilized oocytes. In a further aspect, the method of in vitro embryo production comprising the method of producing embryos, maturing embryos and improving survival of embryos described herein may further include the additional step of embryo transfer and/or cryopreservation for later use after culturing the fertilized oocytes. In another aspect, the method of in vitro embryo production comprising a method of improving viability of embryos post cryopreservation described herein may further include the additional step of embryo transfer after thawing the cryopreserved embryos.

The term "oocyte retrieval" refers to the process of obtaining oocytes. The term "oocyte maturation" refers to the process of maturing oocytes following oocyte retrieval. The term "in vitro fertilization" means a procedure involving incubation of mature oocytes with spermatozoa in culture media to allow fertilization of the oocytes resulting in fertilized oocytes. As used herein the term "thawing" refers the process of preparing a cryopreserved embryo for embryo transfer. As used herein the term "later use" may include embryo transfer.

The steps involved in producing the fertilized oocytes used in the above methods may be prepared using techniques known in the art. For example, oocyte retrieval from a mammal may be accomplished by ultra-sonography guided fine needle aspiration of follicular fluid. Alternatively, oocyte retrieval may be accomplished using other methods known by those skilled in the art such as surgical laparotomy and exteriorization of the ovaries or laparoscopic localization followed by aspiration of follicular fluid. The follicular fluid containing the oocytes may be placed into oocyte collection medium.

Similarly, oocyte maturation may be accomplished using techniques known in the art. For example, mammalian oocytes may be matured by treating the oocytes with IVM media. In one aspect, the IVM media contains protein-free tissue culture medium, steer serum, and may be supplemented with LH, FSH, and estradiol. In another aspect, the IVM media contains protein-free tissue culture medium TCM 199 (Invitrogen); approximately 22-28 mM HEPES, including about 25 mM HEPES; approximately 1.5-2.5% steer serum, including about 2% steer serum (Cansera) and may be supplemented with approximately 0.9-1.1 ug/ml LH, including about 1 ug/ml LH; approximately 0.4-0.6 ug/ml FSH, including about 0.5 ug/ml FSH; and approximately 0.9-1.1 ug/ml estradiol, including about 1 ug/ml estradiol. The oocytes may be incubated at approximately 34-43° C., including about 38.5° C. and approximately 4-6% $CO_2$ in air, including about 5% $CO_2$ in air, for approximately 19-26 h, including about 24 h. In another aspect, oocyte maturation may also be performed using commercial sources of culture media suitable for oocyte maturation.

As used herein "mammalian oocytes" includes bovine, porcine, and preferably human oocytes.

The procedure for in vitro (IVF) of mature oocytes from a mammal may be performed using techniques known in the art. For example, IVF involves sperm capacitation, washing and fertilization in IVF medium. IVF may be performed using commercially available IVF media. In one aspect, IVF media may contain synthetic oviduct fluid supplemented with BSA, amino acids, gentimycine and pyrovate.

In another aspect, the IVCMT disclosed herein may also be applied to improve survival of embryos produced by somatic cell nucleotransfer and cloning.

In a further aspect, the IVCMT disclosed herein may further be applied to the diagnosis of sub-fertility and correlation with thyroid hormone diseases.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The above generally describes the present disclosure. A more complete understanding can be obtained by reference to the following specific examples. These examples are described solely for the purpose of illustration and are not intended to limit the scope of the present disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Analysis of Thyroid Hormone Levels in Follicular Fluid and Serum, and Detection of Thyroid Receptors in Reproductive Tissues Summary Oocytes and embryos are exposed to thyroid hormones within the reproductive tract where oocytes are matured, fertilized and undergo early embryo development, suggesting that this hormone is important for development. Accordingly, bovine follicular fluids from different follicles and serum were analyzed to detect the levels of thyroid hormones in both total and free fractions. The levels of total and free thyroid hormones in the follicles were similar to the serum levels and in the revelatory time there was an increase in the total T4 in serum and active follicles. Expression of thyroid hormone receptors was detected in untreated in vivo immature bovine oocytes, T3/T4 treated mature oocytes, T3/T4 treated eight day old embryos (blastocysts), and harvested in vivo embryos, but not detected in control in vitro eight day old embryos (blastocysts).

Methods

Thyroid Hormone Levels in Follicular Fluid and Serum

Follicular fluid was obtained by aspirating ostensible dominant (DF) and all visible subordinate (SF) ovarian follicles, from freshly killed bovine cows (n=20) during post-mortem examination in an abattoir. From the ovaries, follicular fluid was aspirated from DFs and all visible SFs. From another group of super-ovulated cows (n=15) samples of follicular fluid using ultasonography guided fine needle aspiration and blood by venopuncture were collected at different stages of folliculogenesis. The following sample points were used: serum five days post ovulation (SD5), serum six days post superovulation (SD6S) also known as day 12 post ovulation, ovarian follicular fluid from a dominant follicle six days post superovulation (FFD6S) also known as 12 days post ovulation, ovarian follicular fluid from a dominant follicle five days post superovulation (FFDFD5), ovarian follicular fluid from a subordinate follicle five days post ovulation (FFSF5D). Samples were stored at −20° C. until analyzed by radioimmunoassay to quantify the concentration of thyroid hormones TT3, fT3, TT4, fT4. Statistical significance between groups was determined using a t-test.

Figure 17:
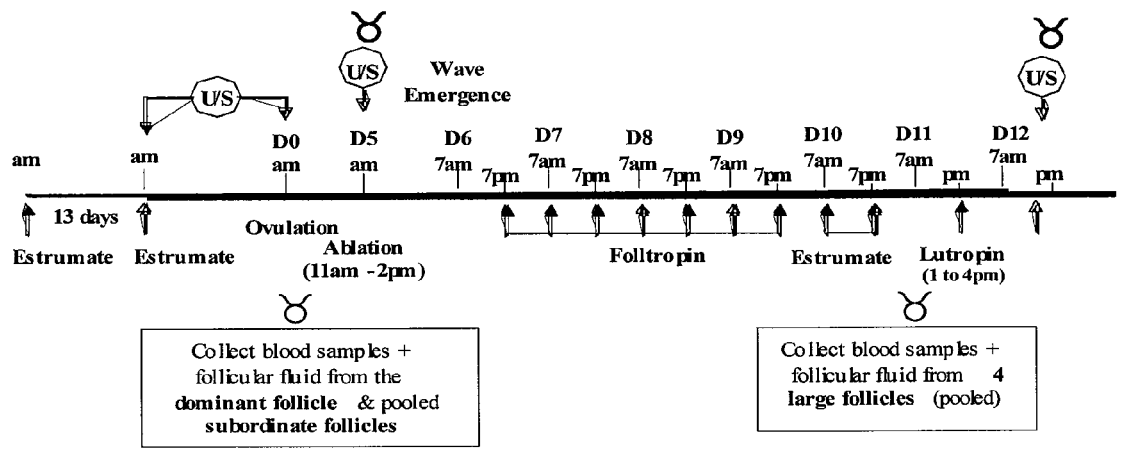
FIG. 17 is a drawing depicting the experimental design of ovulation (D0), superovulation (D12) and oocyte production protocol.

The experimental design of ovulation (D0) and superovulation (D12) and oocyte production protocol is depicted in FIG. 17.

Detection of Thyroid Receptors in Reproductive Tissues

The presence of genetic material (RNA) coding for thyroid hormone receptors was determined in untreated in vivo immature bovine oocytes, control and T3/T4 treated mature oocytes, control and T3/T4 treated eight day old embryos (blastocysts), and untreated in vivo eight day old embryos, using standard methods for RT-PCR. DNA following PCR amplification was separated by mass on a 1DE agarose gel, scanned to create a digitized image and identified visually for presence or absence in comparison to a standardized molecular mass marker.

Results

The thyroid hormone concentration in bovine serum and follicular fluid was determined. The range of the mean concentration of TT4, TT3, fT4, fT3, measured in bovine serum, was 47.3-55.5 nmol/L; 1.5-1.6 nmol/L; 15.6-18.4 pmol/L; 1.5-1.7 pmol/L, respectively (FIGS. 2A, 2B, 3A, 3B). The range of the mean (n=15) concentration of TT4, TT3, fT4, fT3, measured in bovine follicular fluid, was; 31.2-48.7 nmol/L; and 0.9-1.3 nmol/L; 12.6-13.6 pmol/L; 0.2-0.4 pmol/L respectively (FIGS. 2A, 2B, 3A 3B).

Blood samples and follicular fluid samples obtained demonstrated on Day 5 post ovulation, circulating serum $TT_4$ concentrations were greater (P<0.05) than follicular fluid content of $TT_4$ in dominant ($DF_s$) or subordinate antral follicles (SFs). Both $TT_3$ and $fT_3$ concentrations were greater (P<0.05) in serum than in follicular fluid from DFs or SFs. Serum concentrations on day 12 (SD6S) of $fT_4$, $TT_3$ and $fT_3$ were greater (P<0.05) than those in follicular fluid (4 follicles/cow). Serum concentrations of $fT_4$ were greater (P<0.05) on Day 12 (SD6S) than Day 5 (SD5). Analysis of follicular fluid sampled from the post mortem bovine ovaries, did not indicate significant differences (P>0.05) in the concentrations of total and free fractions of thyroid hormones between DFs and SFs.

In summary: 1) the physiological status of bovine antral follicles (i.e., dominant versus subordinate) may affect the accumulation of $TT_4$ in follicular fluid in vivo; 2) hormonal ovarian super-ovulation increases circulating levels of $FT_4$ and $FT_3$ without affecting follicular fluid content of thyroid hormones; and 3) there were no differences in follicular fluid content of thyroid hormones between DFs and SFs in the slaughterhouse ovaries.

Thyroid hormone receptors were identified in untreated in vivo immature bovine oocytes, T3/T4 treated mature oocytes, T3/T4 treated eight day old embryos (blastocysts), and harvested in vivo embryos, but were not detected in control eight day old embryos (blastocysts) (FIGS. 1A, 1B, 1C).

Discussion

Thyroid hormones exist in follicular fluids at levels similar to the serum. Thyroid hormones were present at physiological levels in dominant and super stimulated follicles. Follicles with active steroidogenesis had higher levels of thyroid hormones. A relatively high concentration of thyroid hormones was demonstrated in different stages of the estrous cycle in the follicular fluid (FF) of bovine ovaries routinely used for IVF.

The concentrations of thyroid hormone in follicular fluid and serum and the detection of receptors in the bovine oocytes and embryos illustrate that thyroid hormone is important for normal embryo development in the oviduct and uterus. The absence of thyroid hormone receptors expressed by control embryos suggests that receptor expression is either induced or maintained by external exposure to thyroid hormone.

Example 2

In Vitro Embryo Production Using Embryo Culture Media Containing Thyroid Hormone Summary Bovine oocytes and embryos were treated with embryo culture media containing different concentrations of thyroid hormones and evaluated for embryonic development. Thyroid hormones were added to IVM media, IVF media and IVC media to evaluate the competency of oocytes and embryos at different stages of early embryo development. T3/T4 treated blastocysts were cultured in media that was supplemented with synthetic thyroid hormones, 50 ng/ml T4 and 50 ng/ml T3 during IVM, IVF and IVC. Control blastocysts were cultured during IVM, IVF and IVC in media that did not contain thyroid hormone. Additional time-course experiments were conducted in which the treated groups were cultured in the media supplemented with T3 (50 ng/ml) and T4 (50 ng/ml) only during the IVM or IVC stages, to determine the time of action.

A beneficial effect of the use of culture media containing thyroid hormone during in vitro embryo production was improved viability and survival of bovine embryos as demonstrated in FIGS. 5-8. The data also indicated a cryoprotective effect, including improved viability and survival of frozen-thawed bovine embryos treated with culture media containing thyroid hormone as shown in FIGS. 9 and 10. The data indicated that the benefit of culture media containing thyroid hormone occurs during the in vitro culture (IVC) stage. Use of the culture media containing thyroid hormone only during in vitro oocyte maturation (IVM) (FIG. 11) did not show any differences in in vitro embryo production. In contrast, blastocysts treated with culture media containing thyroid hormone only during IVC (FIG. 12) exhibited beneficial effects similar to those described in FIGS. 6 and 13, in which the culture media containing thyroid hormone was used at all stages (IVM, IVF, IVC) of early embryo development.

Methods

Preparation of Embryo Culture Media for In Vitro Embryo Production

The in vitro culture media used for in vitro embryo production (IVMC) is composed of the following commercially available materials: 10 ml synthetic oviduct fluid (SOF) (BSS0460, Chemicon-Millipore, Billerica, Mass.); 50 ul sodium pyruvate (P4562-5G, Invitrogen, Burlington, ON); 200 ul non essential amino acids 100× (11140050, Invitrogen); 100 ul essential amino acids (11130051, Invitrogen); 5 ul gentamicin (G-1397, Invitrogen); 560 ul EFAF BSA 15% in SOF (A-88096-5G, Sigma-Aldrich, Oakville, ON); and 200 ul bovine steer serum (B15008, PAA Lab formerly Cansera, Rexdale, ON).

Unbound synthetically manufactured T3 and T4, was added to the IVCM media described above to create IVCMT media for in vitro embryo production. Preliminary dose response and time course studies were completed using IVCM with thyroid hormone added (IVCMT). IVCMT was used in experiments with bovine embryos, to determine the range of concentrations and time of action of thyroid hormone supplementation, necessary to produce the beneficial effects.

Experiments were completed with thyroid hormones added to IVCM media at doses of 20, 50 and 100 ng/ml. However, results did not vary indicating a lack of dose dependency for this range as well. Consequently, a dose of 50 ng/ml T3 and 50 ng/ml T4 was chosen to demonstrate the benefits of IVCMT media for in vitro embryo production. This concentration is significantly above physiological levels measured in serum and follicular fluid (FIGS. 2-3) but was necessary due to the reduced bioavailability of thyroid hormone when used in vitro compared to in vivo. This is due to the binding of thyroid hormone to BSA, the plastic wall of research vessels, and the absence of active hemostasis to control thyroid hormone concentrations within physiological limits. It is particularly relevant to note that the laboratory standard for culture systems in the present disclosure, as with most of those reported in the literature is based on a defined media with little or no biological supplementation.

The IVCMT used for in vitro production of embryos is composed of IVCM with added 50 ng/ml T4 (T2501, L-Thyroxine sodium salt pentahydrate, Sigma-Aldrich, Oakville, ON) and 50 ng/ml T3 (T6397 3,3',5-Triiodo-L-thyronine sodium salt powder, cell culture tested, Sigma-Aldrich).

In Vitro Embryo Production

Approximately 1600 oocytes underwent the IVM, IVF and IVC protocol to produce embryos in vitro in two treatment groups. The treated group used IVM media, IVF media, and IVC media supplemented with 50 ng/ml T3 and 50 ng/ml T4. (FIGS. 4-10 and 13). In other time-course experiments, treated groups used T3 and T4 supplementation only in IVM media or only in IVC media (FIGS. 11 and 12, respectively) while all control groups used IVM media, IVF media, and IVC media without thyroid hormone supplementation.

Oocyte Collection

Bovine ovaries were collected postmortem in the morning and placed into PBS at 33-37° C. for 0.5-1 h during transport to the lab where they were incubated at 37° C. for 1 h. The ovarian follicles were aspirated using an 18 gauge needle and follicular fluid was collected with suction into a 15 ml vacutainer tube. The follicular fluid was placed into fresh oocyte collection medium (Hams F10) and oocytes were retrieved under microscopy. Oocytes were washed in oocyte medium which contains protein-free tissue culture medium TCM 199 (Invitrogen), with added 25 mM HEPES, and 2% steer serum (Cansera)) and then washed in IVM media which is composed of TCM 199, with added 25 mM HEPES, 2% steer serum (Cansera), 1 ug/ml luteinizing hormone (LH), 0.5 ug/ml follicular stimulating hormone (FSH) (Bioniche, Belleville, ON), and 1 ug/ml estradiol (E2) (Veterinary Chiron, Guelph, ON). Then grade 1 oocytes having multiple layers of cumulus cells were selected. Groups of 20 control or treated oocytes were placed in to drops (80 ul under mineral oil) of IVM media or IVM supplemented with 50 ng/ml T3 and 50 ng/ml T4, respectively.

Oocyte Maturation

Oocytes were matured by placing them into IVM media. The oocytes were incubated at 38.5° C. and 5% $CO_2$ in air for 22-24 h until mature. Oocytes were washed twice in Hepes-TALP and twice in IVF-TALP and transferred from IVM drops through two washes of Sperm-TALP and two washes of IVF-TALP into IVF drops (80 ul IVF-TALP under filtered oil).

In Vitro Fertilization

Semen capacitation occurred in Sperm-TALP medium. After oocyte maturation and prior to insemination 2-3 straws of frozen semen were thawed in a 33-36° C. water bath for 10-20 seconds and placed in equilibrated Sperm-TALP at 38.5 C for 1 hour to allow sperm to swim upwards. The top portion (~1 ml) of from each tube containing live sperm was aspirated and combined, washed with fresh Sperm-TALP (10 mls), centrifuged (200 g, 10 min), supernatant discarded and the remaining combined swimming-up sperm sample was assessed for motility and concentration. This sperm solution (10 ul, $10^6$ sperm/ml) was added to mature oocytes (~20) contained in 80 ul of IVF-TALP ( ) in the control group and IVF-TALP supplemented with 50 ng/ml T3 and 50 ng/ml T4 in the treated group. Both are incubated at 38.5° C. and 5% $CO_2$ in air for 18 h. Presumptive zygotes are removed by centrifugation, washed three times in Sperm-TALP followed by three washes in IVCM to prepare for IVC.

In Vitro Culture

The control and treated zygotes (30 ul per 30 zygotes) were transferred into IVCM and IVCMT, respectively, and incubated at 38.5° C. and 5% $CO_2$ in air for 7 days.

Evaluating Embryonic Competency and Development

Cleavage rates were assessed at 36 hours post insemination (hpi), by counting embryos with inversion in the zona pellucida and with 2 or more cells. Cleavage of an embryo cannot occur without prior fertilization of an oocyte, therefore an assessment of cleavage rate is also an assessment of the fertilization rate.

On day 8 after fertilization or 192 hpi, blastocysts were harvested from each group to assess blastocyst formation and hatching rates. Embryos with a ruptured or detached zona pellucida were considered hatched while embryos containing a visible blastocyst were considered a blastocyst. The hatching and blastocyst formation rates (percentage) in treated and control groups were calculated for each trial and for the overall mean of all 8 trials and differences between groups were analyzed for statistical significance using nonparametric analysis with an exact Wilcoxon (ranksum) test. Embryo quality (apoptosis) was assessed using terminal deoxynucleotidyl transferase dUTP nick end labeling (TUNEL) assay which identifies fragmented DNA. On day 8, 192 hpi, a subset of embryos were chosen from each trial and group to represented the best quality same size embryos (blastocysts). These 10-18 blastocysts from each group, were fixed in 1% para-formaldehyde and stained in situ with fluorescein (Roche, Germany) for defragmentation of DNA as a marker of apoptosis (cell death). Nuclei were counter-stained with propidium iodide as a marker of total cell numbers per blastocyst. The apoptosis rate (percentage) was calculated and the total cell number was counted, per blastocyst, and the mean calculated for each trial and for all trials combined. Statistical significance was calculated using an exact Wilcoxon test.

Cryopreservation

After the blastocysts were harvested, the embryos were cryopreserved in the cryopreservation media described below.

Cryopreservation Media

Modified D-PBS with serum solution (DPBSS) contains: commercially available modified D-PBS (450-1500, Glbco,) (1 g/l of d-glucose, 5 ug/l phenol red, and 36 mg/l sodium pyruvate, with Ca++ and Mg++, 1% Pen-Strep with added 10% (v/v) bovine steer serum (Cansera). Ethylene Glycol 1.5M solution (EG) contains: 0.93 gm ethylene glycol per 10 ml of DPBSS.

Cryopreservation Procedure

DPBSS and EG solutions are warmed to room temperature. Straws (0.25 ml) are loaded with one long column of DPBSS and 2 short columns of EG. Embryos are selected from their culture drops and rinsed in PBSS, then added to a 35 mm dish containing 2.5 ml of EG solution. The timer is activated when embryos are added to EG. Using a fine glass pipette, embryos are placed into a second drop of EG within the straw. A final volume of DPBSS is drawn up into the straw which is heat sealed. Within 10 minutes of exposure to EG, embryos are placed into an alcohol bath of FTS freezer, previously equilibrated to −7° C. After 5 minutes at −7° C. straws are seeded using a thin spatula cooled in liquid nitrogen, and the selected program to decrease the temperature at a rate of 0.3° C. per minute is started, after a total of 10 minutes at 7° C. After the program is completed and straws reach −35° C. and held for 0-10 min, straws are plunged into liquid nitrogen.

Thawing Procedure

Straws are thawed rapidly for 5 seconds in air followed by 15 seconds in a 35° C. water bath. Thereafter, all steps are carried out in a warm (30 to 33° C.) hood. The contents of the straw are expelled into an empty petri dish. The embryos are picked out and washed in 2.5 ml of DPBSS, and then washed twice in IVCM. Embryos from both control and treated groups were placed into drops of IVCM without the addition of thyroid hormones or analogues thereof, and cultured for 72 h. IVCM drops are prepared 1 to 3 hr. ahead of use.

Evaluating Survival of Thawed Cryopreserved Embryos

Thawed cryopreserved embryos were evaluated for survival post cryopreservation. When embryos are cryopreserved, they become smaller and develop a compact morphology unlike a blastocyst. Viable thawed embryos expand from the compact form and return to a multicellular morphology with clear cytoplasm, identical to blastocysts prior to cryopreservation. Nonviable (dead) embryos remain compact and smaller than viable embryos and have fragmented cytoplasm which does not resemble a blastocyst. The morphology of all of the thawed embryos was inspected 24 h after thawing to assess viability and calculate a survival rate. The embryos were inspected again at 72 h after thawing to assess hatching. Statistical significance was calculated using an exact Wilcoxon test.

Results

Figure 4A:
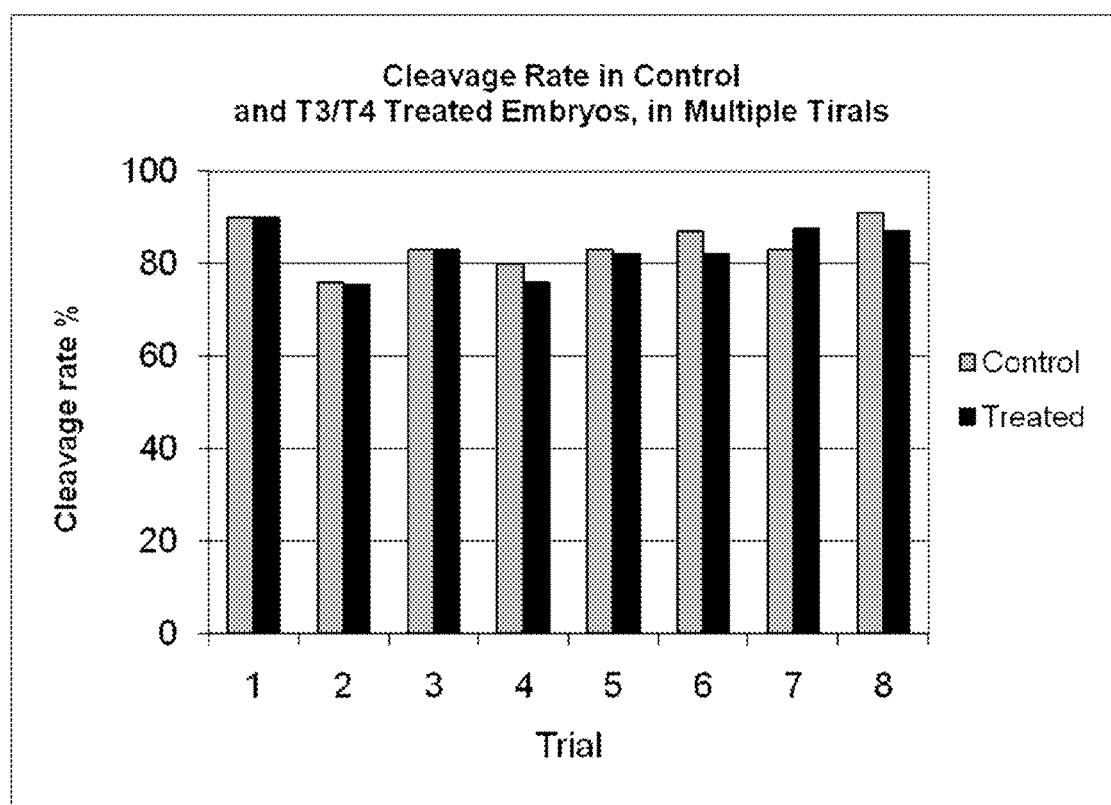
FIG. 4A is a graph showing the cleavage rate in control and T3/T4 treated bovine embryos, from multiple repeated trials.
Figure 4B:
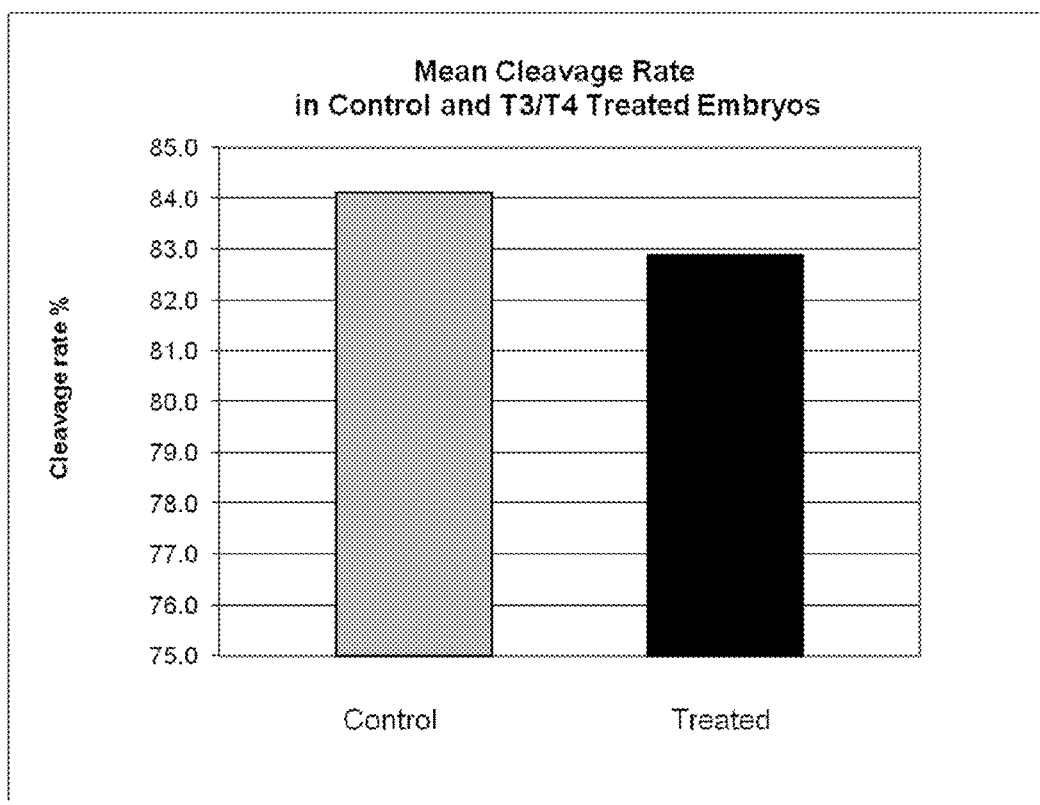
FIG. 4B is a graph showing the mean cleavage rate in control and T3/T4 treated bovine embryos (n=877 controls, n=900 treated).
Figure 5A:
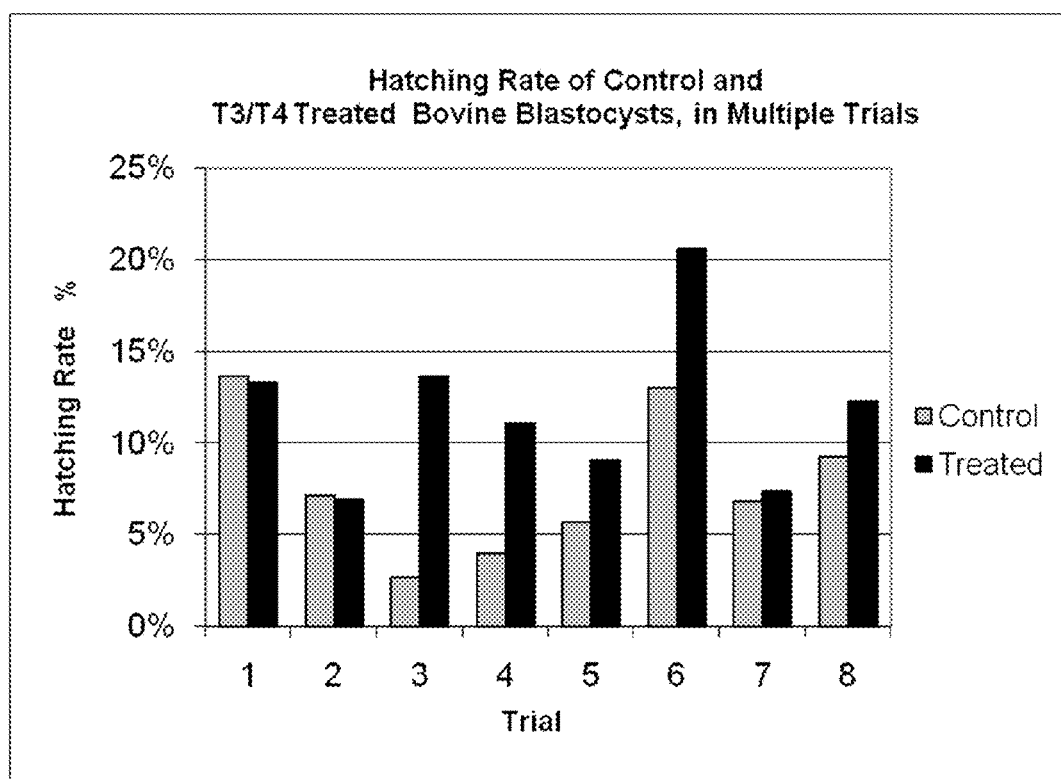
FIG. 5A is a graph showing the hatching rate in control and T3/T4 treated bovine blastocysts, from multiple repeated trials.
Figure 5B:
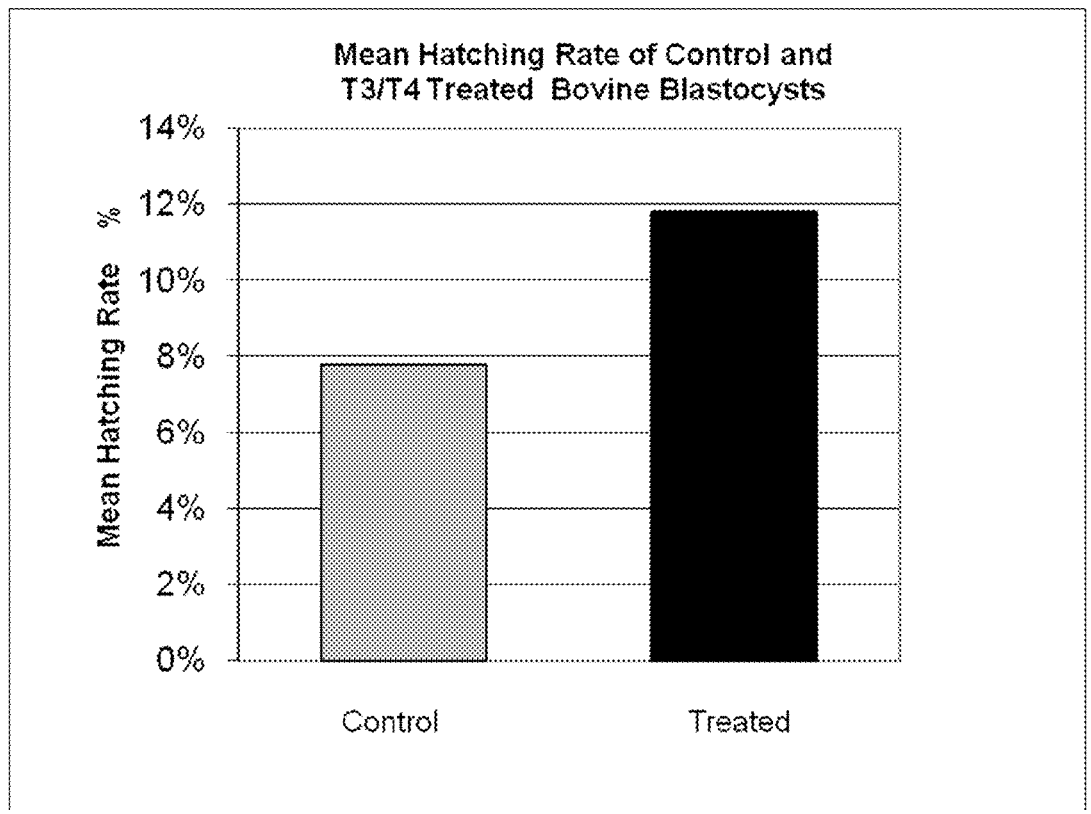
FIG. 5B is a graph showing the mean hatching rate in control and T3/T4 treated bovine blastocysts (n=271 controls, 333 treated).
Figure 6A:
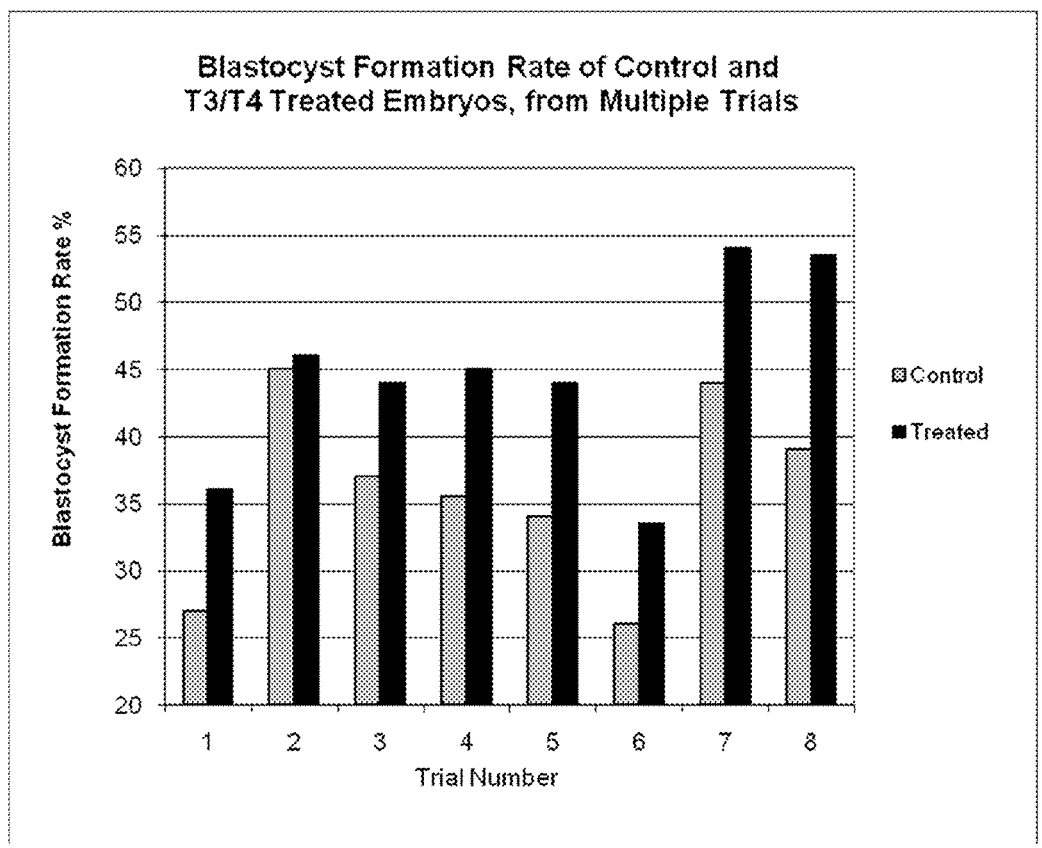
FIG. 6A is a graph showing the blastocyst formation rate in control and T3/T4 treated bovine blastocysts from multiple repeated trials.
Figure 6B:
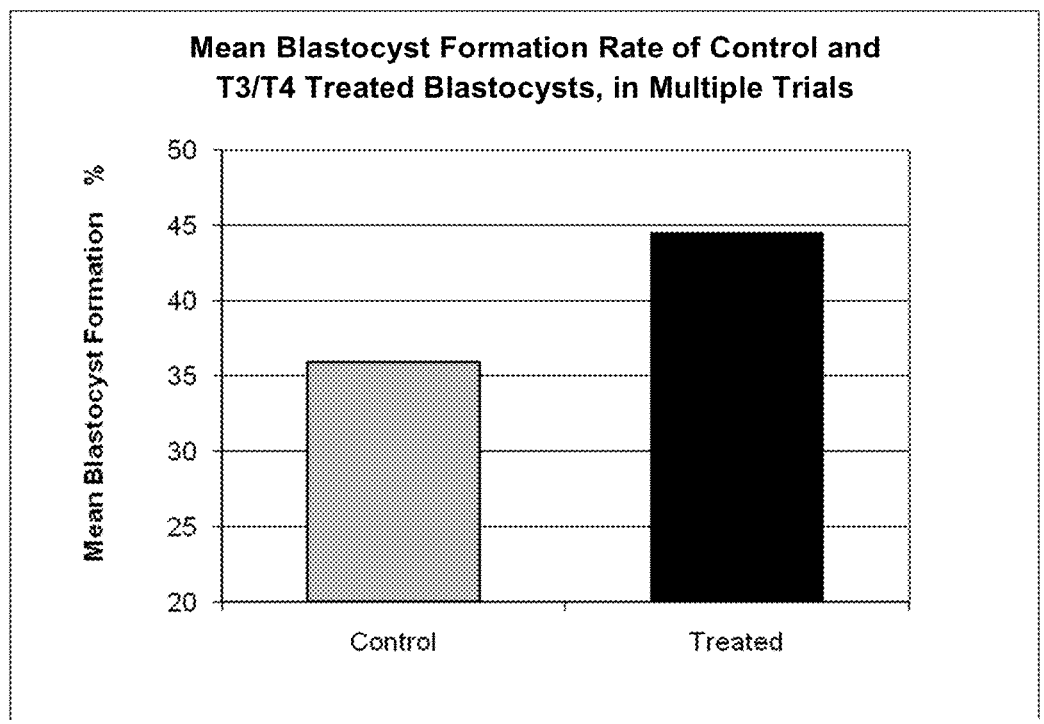
FIG. 6B is a graph showing the mean blastocyst formation rate in control and T3/T4 treated bovine blastocysts (n=271 controls, 333 treated).
Figure 7A:
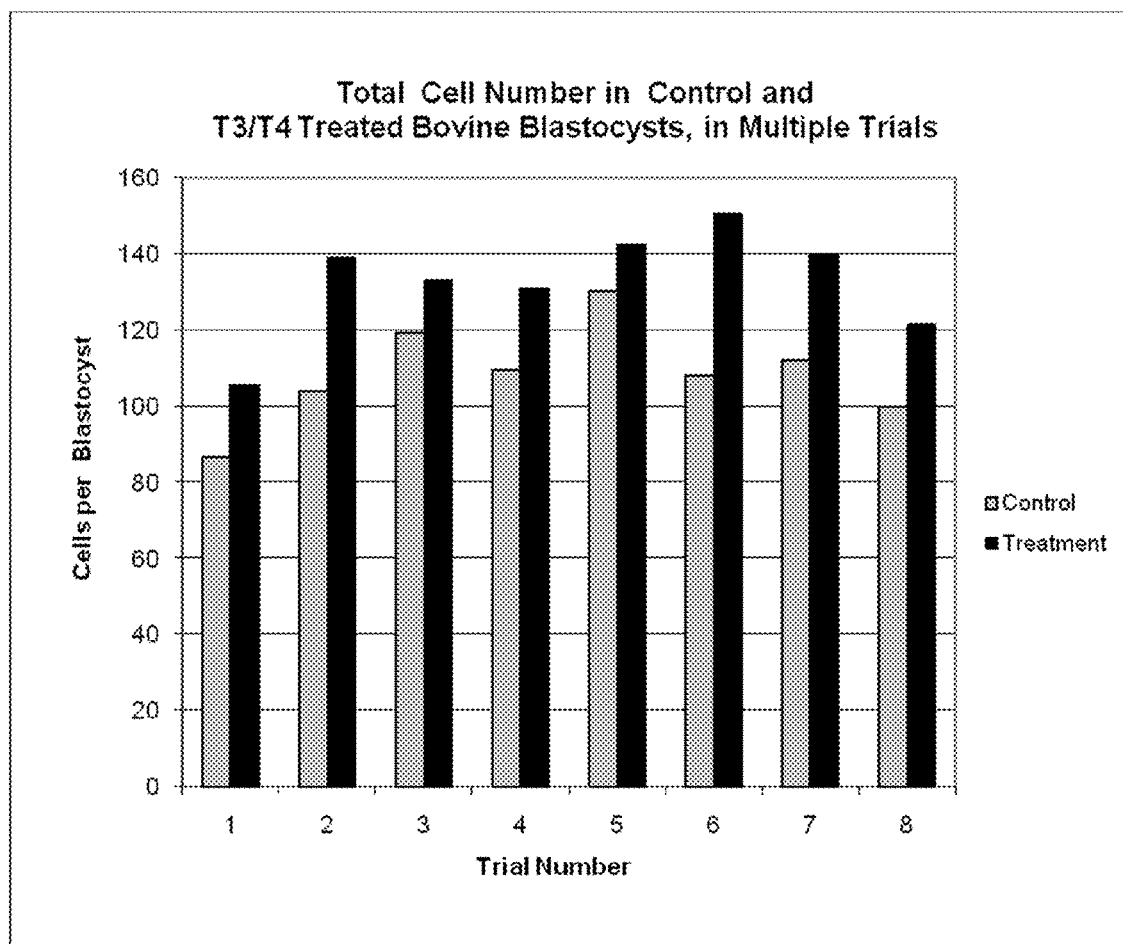
FIG. 7A is a graph showing the total number of cells in control and T3/T4 treated bovine blastocysts, from multiple repeated trials.
Figure 7B:
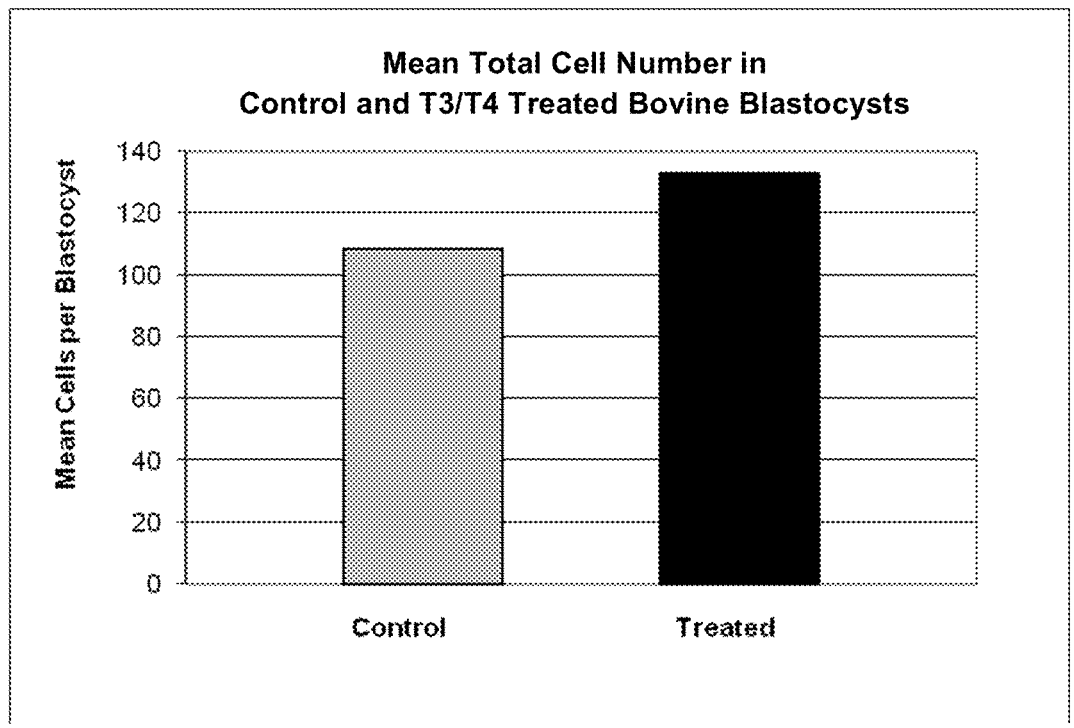
FIG. 7B is a graph showing the mean total number of cells in control and T3/T4 treated bovine blastocysts (n=83 controls, 79 treated).
Figure 8A:
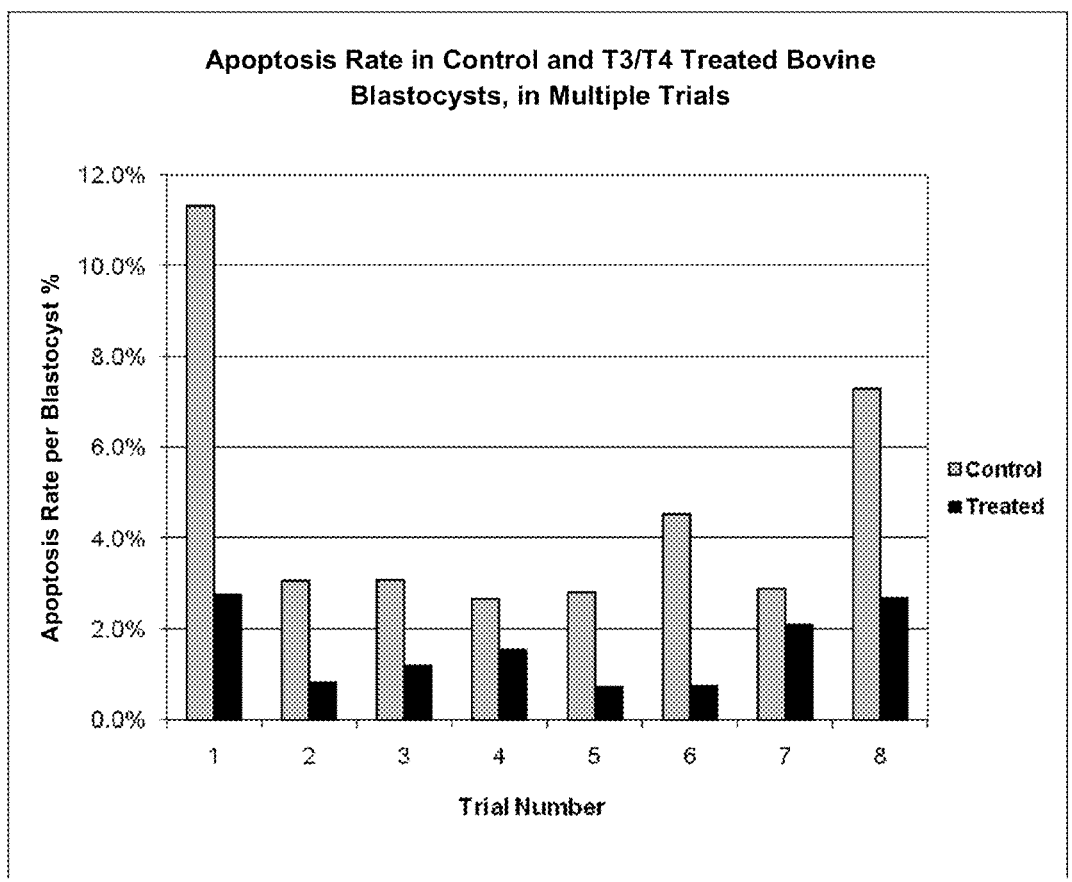
FIG. 8A is a graph showing the apoptosis rate in control and T3/T4 treated bovine blastocysts, from multiple repeated trials.
Figure 8B:
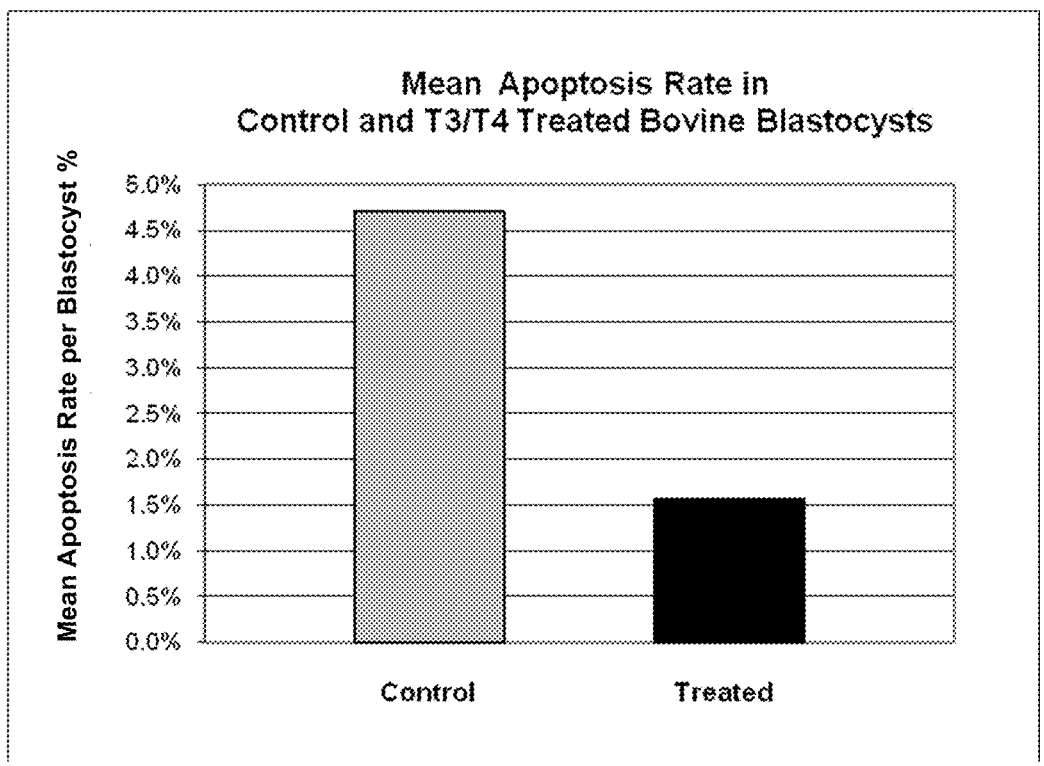
FIG. 8B is a graph showing the mean apoptosis rate in control and T3/T4 treated bovine blastocysts (n=83 controls, 79 treated).
Figure 9A:
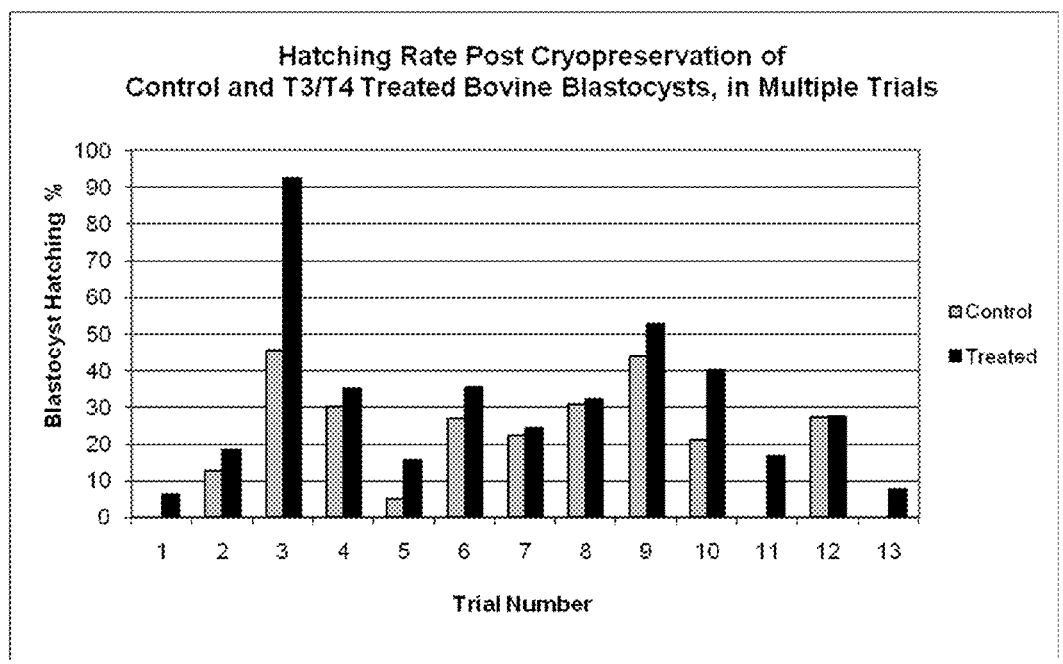
FIG. 9A is a graph showing the hatching rate post cryopreservation of control and T3/T4 treated bovine blastocysts, from multiple repeated trials.
Figure 9B:
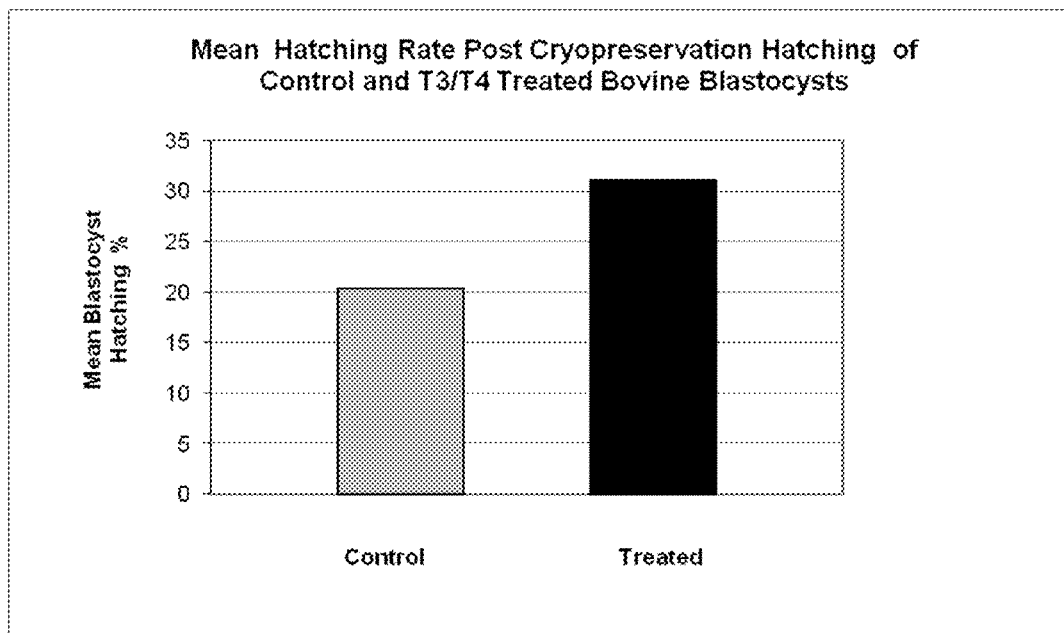
FIG. 9B is a graph showing the mean hatching rate post cryopreservation of control and T3/T4 treated bovine blastocysts, (n=277 controls, 284 treated).

The studies showed the blastocyst rate was significantly increased (+10%, p=0.02) in the treated group compared to controls (FIGS. 6A, 6B). Also, the total number of cells per blastocyst was significantly increased (+22%, p=0.001) in the treated group relative to controls (FIGS. 7A, 7B). The hatching rate of blastocysts in the treated group was also greater (+51%, p=0.04) relative to controls (FIGS. 5A, 5B) while the apoptosis rate in the treated group was significantly decreased (−58%, p=0.001) compared to the control group (FIGS. 8A, 8B). The data did not show significant differences in cleavage rates between control and treated groups (FIGS. 4A, 4B). Dose response experiments were conducted with a lesser number of embryos (data not shown) and the beneficial effects stated above were identical for media supplemented at all stages with T3 and T4 over the range of 20 ng/ml to 100 ng/ml.

Figure 11:
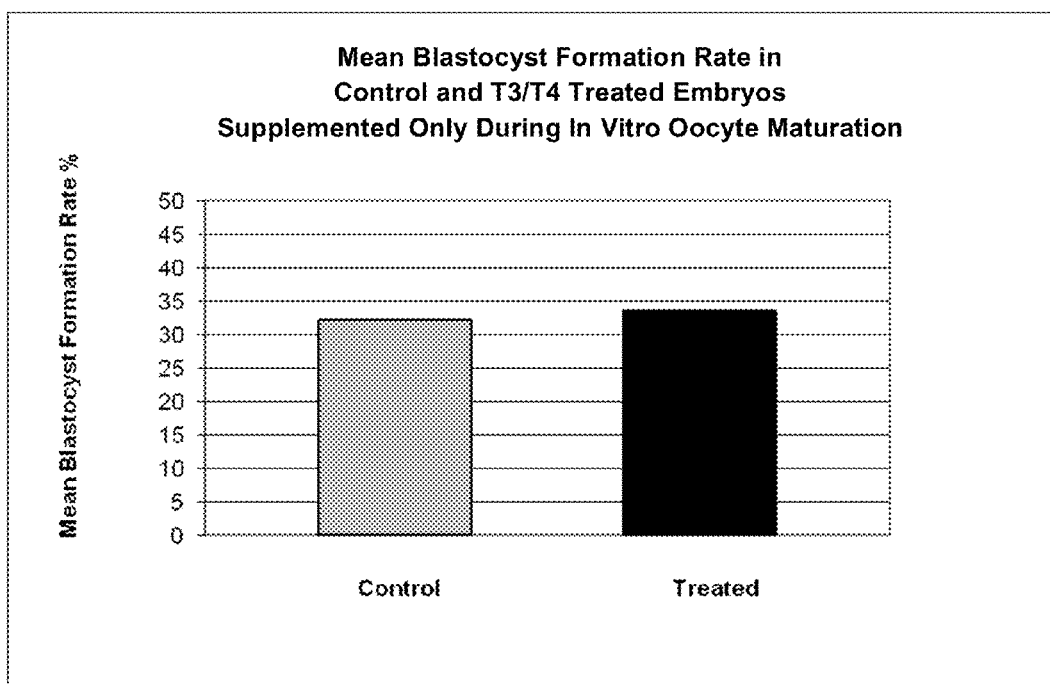
FIG. 11 is a graph showing the mean blastocyst formation rate of control bovine blastocysts and those treated with T3/T4 only during in vitro oocyte maturation (IVM) (n=514 controls, 496 treated).
Figure 12:
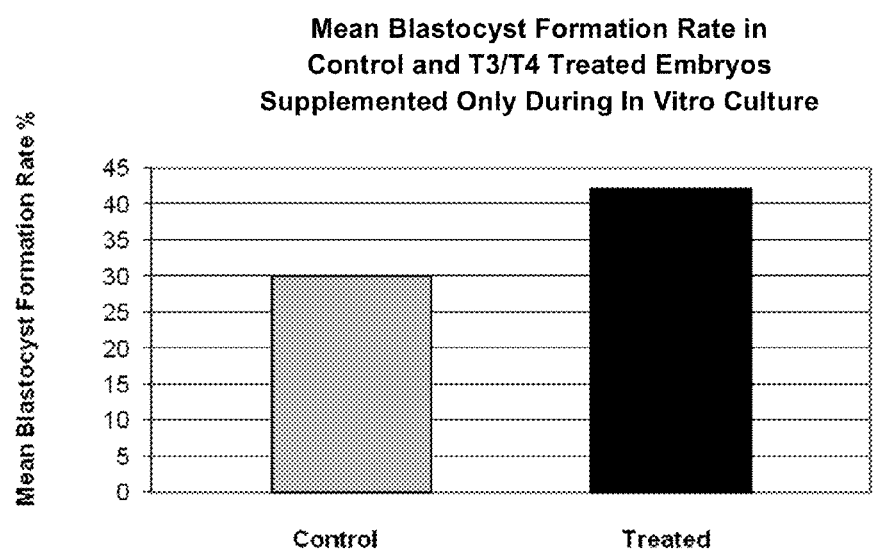
FIG. 12 is a graph showing the mean blastocyst formation rate of control bovine blastocysts and those treated with T3/T4 only during in vitro embryo culture (IVC) (n=737 controls, 716 treated).
Figure 13:
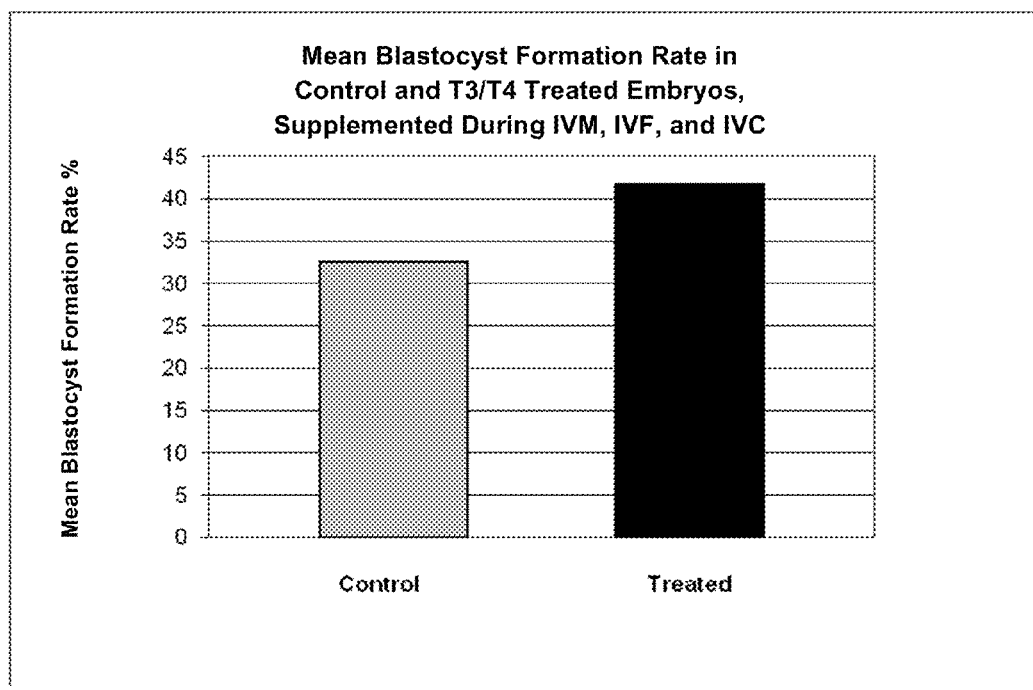
FIG. 13 is a graph showing the mean blastocyst formation rate of control bovine blastocysts and those treated with T3/T4 during IVM, IVF, IVC (n=873 controls, 858 treated).

Use of the culture media containing thyroid hormone only during in vitro maturation (IVM) (FIG. 11) did not show any significant differences in blastocyst formation rate (p=0.46). Blastocysts treated with culture media containing thyroid hormone only during IVC (FIG. 12) exhibited significant beneficial effects with respect to blastocyst formation rates (p=0.001), comparable to the beneficial effects observed when culture media containing thyroid hormone was used at all stages (IVM, IVF, IVC) of early embryonic development (FIG. 6, p=0.02; FIG. 13, p=0.005).

Figure 10A:
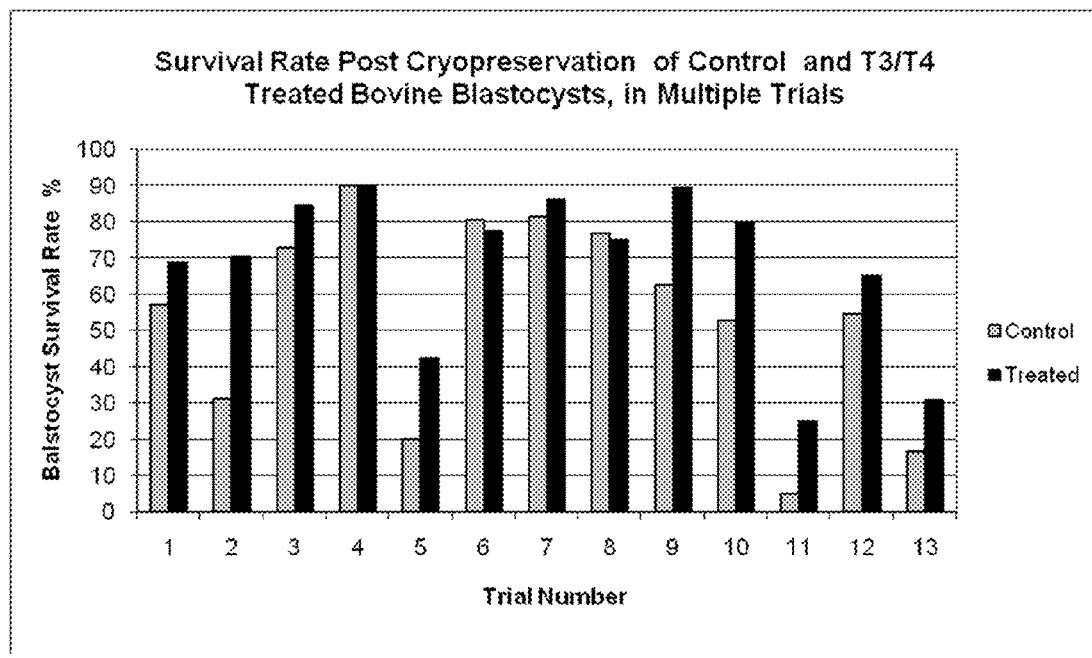
FIG. 10A is a graph showing the mean survival rate post cryopreservation of control and T3/T4 treated bovine blastocysts, from multiple repeated trials.
Figure 10B:
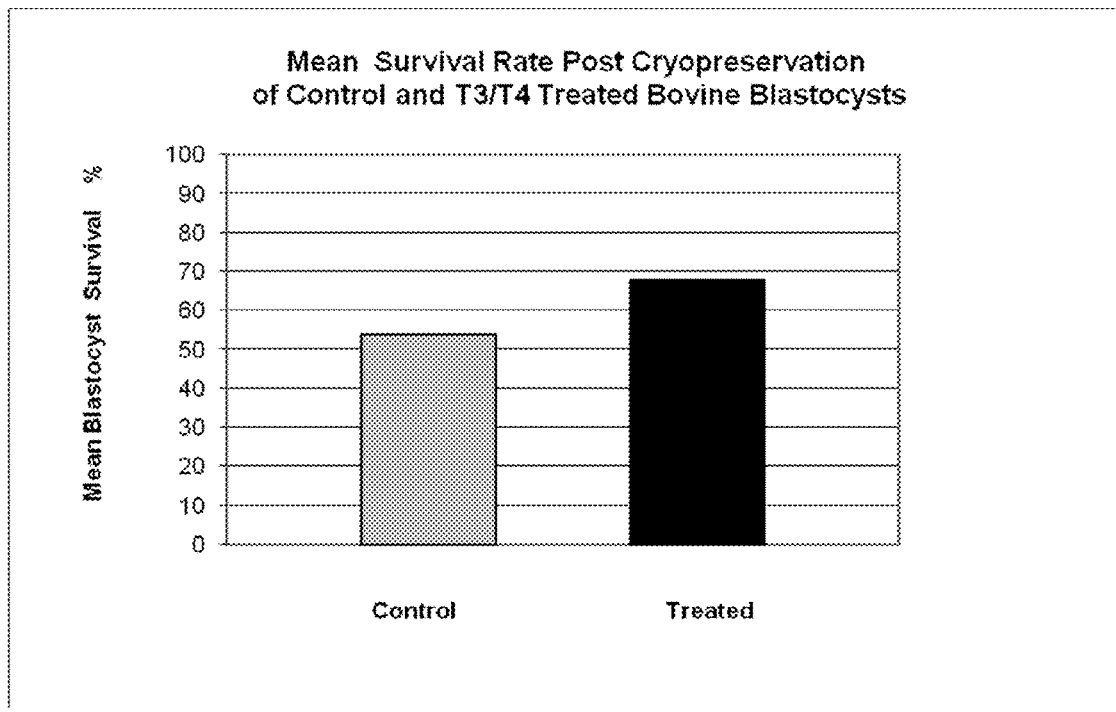
FIG. 10B is a graph showing the mean survival rate post cryopreservation of control and T3/T4 treated bovine blastocysts (n=277 controls, 284 treated).

Improved viability of frozen-thawed bovine embryos treated with culture media containing thyroid hormone was demonstrated by improved blastocyst hatching rates (FIGS. 9A, 9B, p=0.003) and survival rates (FIGS. 10A, 10B, p=0.01).

Discussion

A beneficial effect of embryo culture media containing thyroid hormone on in vitro embryo production was identified. The application of embryo culture media containing T3 and T4 to in vitro embryo production alters the competency of early embryo development, maturation and survival. Thyroid hormones exert their effect through different pathways, including mitochondrial, transcriptional and post-transcriptional mechanisms in early embryo development.

Treatment of embryos with T3 and T4 increased blastocyst formation rate. Treatment of oocytes only during IVM (FIG. 11) did not reproduce the beneficial effects. However, treatment of blastocysts only during the IVC stage (2 cell to >32 cell embryo; FIG. 12), reproduced the beneficial effects observed when media was supplemented with T3 and T4 at all stages (FIGS. 6 and 13). This data suggests that supplementation during in vitro embryo culture (IVC), and not oocyte maturation (IVM), nor in vitro fertilization (IVF), is the time period when thyroid hormones cause a beneficial effect on in vitro embryo production. Both T3 and T4 were added, however adding only T3 may be sufficient. The effects do not appear to be dose dependent.

A cryoprotective effect was identified for frozen-thawed embryos treated with the embryo culture media containing thyroid hormones prior to cryopreservation.

While not wishing to be bound by a particular theory, the mechanism which improves embryo survival may be linked to the action of thyroid hormone on the mitochondria of the embryo. Unavoidably, during cryopreservation, mitochondria are damaged and have increased porosity which causes the release of free radical and oxidative species. Mitochondria are one of the key triggers for apoptosis. Therefore anything which can stimulate mitochondria to up regulate and prevent initiating apoptosis would increase embryo survival. Because mitochondria manufacture energy for use by cells we propose that thyroid hormones may change the ATP content of treated embryos to provide more energy for embryo metabolism and post cryopreservation development. More energy utilization results in improved survival.

Future studies include determining: 1) the level of gene expression in different stages of embryo development in control versus treated groups as an indicator for transcriptional effects; 2) the effect of thyroid hormones on mitochondria as a primary site of thyroid hormone action for both transcriptional and non-transcriptional effects; 3) metabolic effect of thyroid hormones on embryos via parameters related to oxidative pathways like ATP production and oxygen consumption; 4) the changes in birth rates and neonatal phenotype in control and treated groups allowed to develop and live a normal lifespan.

Example 3

In Vitro Production of Porcine Embryos

Summary

Porcine oocytes and embryos were treated with embryo culture media containing thyroid hormones and evaluated for embryonic development. Thyroid hormones were added to IVM media, IVF media and IVC media to evaluate the competency of oocytes and embryos at different stages of early embryo development. T3/T4 treated blastocysts were cultured in media that was supplemented with synthetic thyroid hormones, 50 ng/ml T4 and 50 ng/ml T3 during IVM, IVF and IVC. Control blastocysts were cultured during IVM, IVF and IVC in media that did not contain thyroid hormone. A beneficial effect of the use of culture media containing thyroid hormone during porcine in vitro embryo production was improved viability and survival of porcine embryos as demonstrated in FIGS. 15 and 16.

Methods

Preparation of Porcine In Vitro Embryo Culture Media

The porcine in vitro culture media (PIVCM) used for in vitro porcine embryo production was a PZM-3 medium constructed as follows: 108 mM NaCl (Sigma S 7653-250G), 10 mM KCl (Sigma P9541-500G), 0.35 mM KH2PO (Sigma P5655-100G), 0.4 mM MgSO4.7H20 (Sigma M5921-500G), 25.07 mM NaHCO3 (Sigma S6297-250G), 0.20 C3H3O3Na (Na-Pyruvate) (Sigma P8574-5G), 2 mM Ca-(lactate) 2.5H2O (Sigma C8356-250G), 1 mM C5H10N2O3 (L-Glutamine) (Sigma G3126-100G), 5 mM Hypotaurine (Sigma H1384-104G), Basal medium Eagle amino acids (Sigma B6766)/BME (20 ml/L). Minimum medium nonessential amino acids (Sigma M7145) (10 ml/L MEM), Gentamicin (0.05 mg/ml) (Sigma G1397-104G), Fatty acid-free BSA (3 mg/ml) (Sigma A8806-5G).

Unbound synthetically manufactured T3 and T4, was added to the PIVCM described above to create the application media called porcine in vitro media containing thyroid hormone (PIVCMT) for in vitro embryo production. Preliminary dose response and time course studies were completed (data not shown) using PIVCMT as described in previously for bovine embryos. PIVCMT was used in experiments with porcine embryos, to determine the action of thyroid hormone supplementation, necessary to produce the beneficial effects.

The PIVCMT used for in vitro production of embryos is composed of PIVCM with added 50 ng/ml T4 (T2501, L-Thyroxine sodium salt pentahydrate, Sigma-Aldrich, Oakville, ON) and 50 ng/ml T3 (T6397 3,3',5-Triiodo-L-thyronine sodium salt powder, cell culture tested, Sigma-Aldrich). The thyroid hormone used was identical in composition, manufacturer and lot number as that used for the bovine experiments.

In Vitro Embryo Production

In a total of three trials, 893 oocytes underwent the IVM, IVF and IVC protocol to produce embryos in vitro in two treatment groups. The treated group (n=448) used IVM media, IVF media, and IVC media supplemented with 50 ng/ml T3 and 50 ng/ml T4. This disclosure is focused on the use of media specifically during IVC and is called PIVCMT and is described above. The control group (n=445) used IVM media, IVF media, and IVC media without thyroid supplementation.

Oocyte Collection

Ovaries of prepubertal gilts were collected postmortem in the morning and placed into PBS at 33-37° C. for 1 h during transport to the lab where they were incubated at 37° C. for 1 h. Cumulus-oocyte complexes (COCs) were aspirated from 3-6 mm diameter follicles from ovaries of prepubertal gilts using an 18-gauge needle attached to a 10 ml disposable syringe. After collection, COCs were allowed to settle for 20 min and then washed twice in Tyrode's Lactate-Pyruvate-HEPES medium (TLP-HEPES: 5 mM glucose, 113 mM NaCl, 3.2 mM KCl, 0.5 mM MgCl2, 0.4 mM NaH2PO4, 2 mM NaHCO3, 20 mM lactate, 10 mM HEPES and 0.3% Polyvinyl Alcohol, pH 7.4) at 35° C. Only COCs surrounded by a minimum of three cumulus cell layers, with an evenly granulated cytoplasm were selected for IVM.

Oocyte Maturation

Groups of 50 COCs were matured in 4-well dishes (Nunclon Multidishes; Nalge Nunc International, Denmark) containing 0.5 ml of maturation medium (TCM199; Gibco, Invitrogen life technologies, Burlington, ON, Canada), supplemented with 0.1% polyvinyl alcohol (PVA), 0.1 mg/ml cysteine, 10 ng/ml epidermal growth factor (EGF; Gibco), 0.91 mM sodium pyruvate, 3.05 mM D-glucose, 0.5 mg/ml Luteinizing Hormone (SIOUX Biochemical Inc., IA, USA), 0.5 mg/ml Follicle-Stimulating Hormone (SIOUX), and 50 mg/ml gentamicin (Gibco) in a humidified atmosphere of 5% CO2 (v/v) and 95% air at 38.5° C. After 22-24 h of maturation, COCs were transferred to fresh IVM medium without LH and FSH for an additional 20-22 h under the same conditions.

In Vitro Fertilization

After IVM, cumulus cells were removed as described above and oocytes were washed three times in IVF medium (113.1 mM NaCl, 3.0 mM KCl, 7.5 mM CaCl22H2O, 20.0 mM Tris, 11.0 mM glucose, 5.0 mM sodium pyruvate, 1 mM theophiline and 0.1% BSA) (Abeydeera and Day 1997). Groups of 25 to 30 oocytes were then placed into 95 µl droplet of IVF medium covered with embryo tested mineral oil. Dishes were maintained in the incubator for approximately 30 min during sperm preparation. Sperm was prepared from fresh semen using the sperm-rich fraction of the ejaculate collected from a fertile boar. A semen sample of 25 ml was diluted (1:1) with Beltsville thawing solution (BTS) and maintained for 18-22 h at room temperature (20-22° C.) before use. The semen was then centrifuged (80×g) for 3 min and a 2 ml sample from the top collected. The sample was washed twice by centrifugation at 500×g for 3 min in PBS supplemented with 0.1% BSA. The sperm pellet was resuspended in IVF medium and the concentration was adjusted to 10×106 cells/ml. Oocytes were fertilized with 5 ml of sperm solution added to the 95 ml droplets to give a final concentration of 5×105 sperm/ml. Oocytes were co-incubated with the sperm for 6 h. After this period, oocytes were collected from the IVF droplets, washed twice to remove attached sperm cells and cultured in PZM-3 medium.

In Vitro Embryo Culture

The control and treated fertilized oocytes (embryos) were transferred into PIVCM and PIVCMT, respectively, and incubated at 38.5° C. and 5% $CO_2$ in air for 7 days.

Evaluating Embryonic Competency and Development

Cleavage rates were assessed at 36 hours post insemination (hpi), by counting surviving fertilized oocytes with inversion in the zona pellucida and with 2 or more cells. On day 7 after fertilization, surviving blastocysts (n=25 control, n=34 treated) were harvested from each group to assess blastocyst formation. Embryos containing a visible blastocyst were considered a blastocyst. The blastocyst formation rates (percentage) in treated and control groups were calculated for each trial. Nuclei were counter-stained with propidium iodide and nuclei were counted to determine the cell numbers per blastocyst and the overall mean calculated for the three trials combined.

Results

Figure 14:
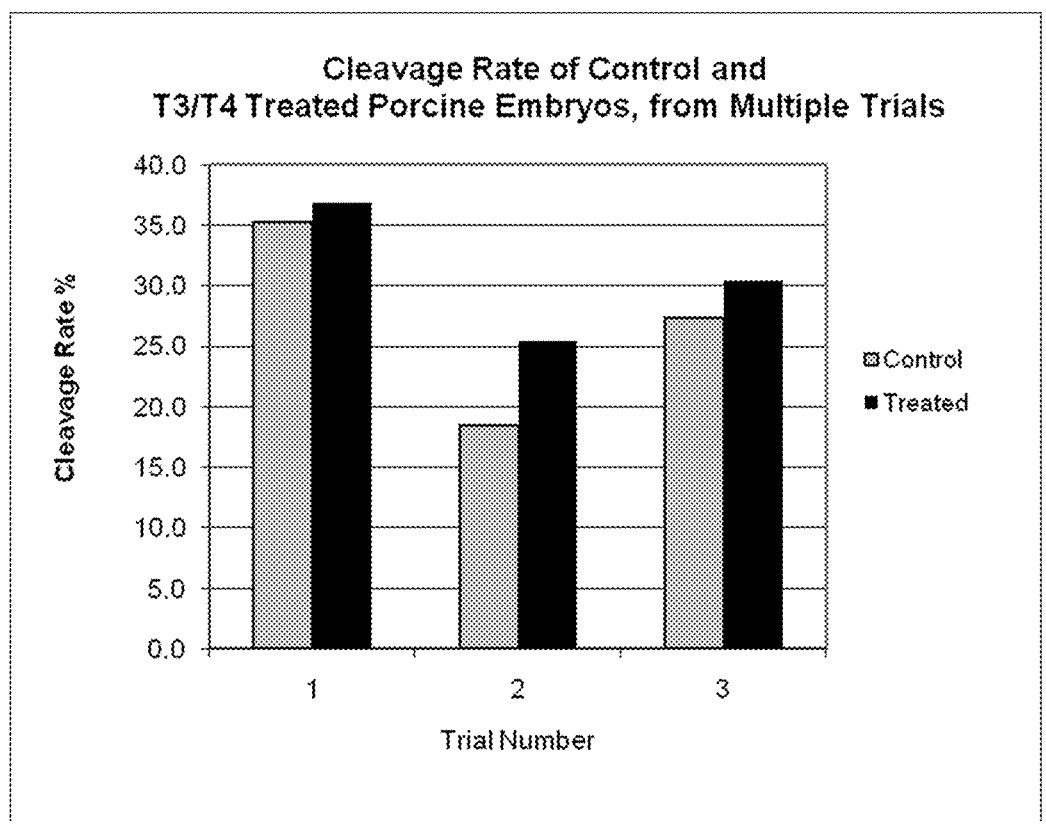
FIG. 14 is a graph showing the cleavage rate in control and T3/T4 treated porcine embryos (n=114 controls, 134 treated), from multiple repeated trials.
Figure 15:
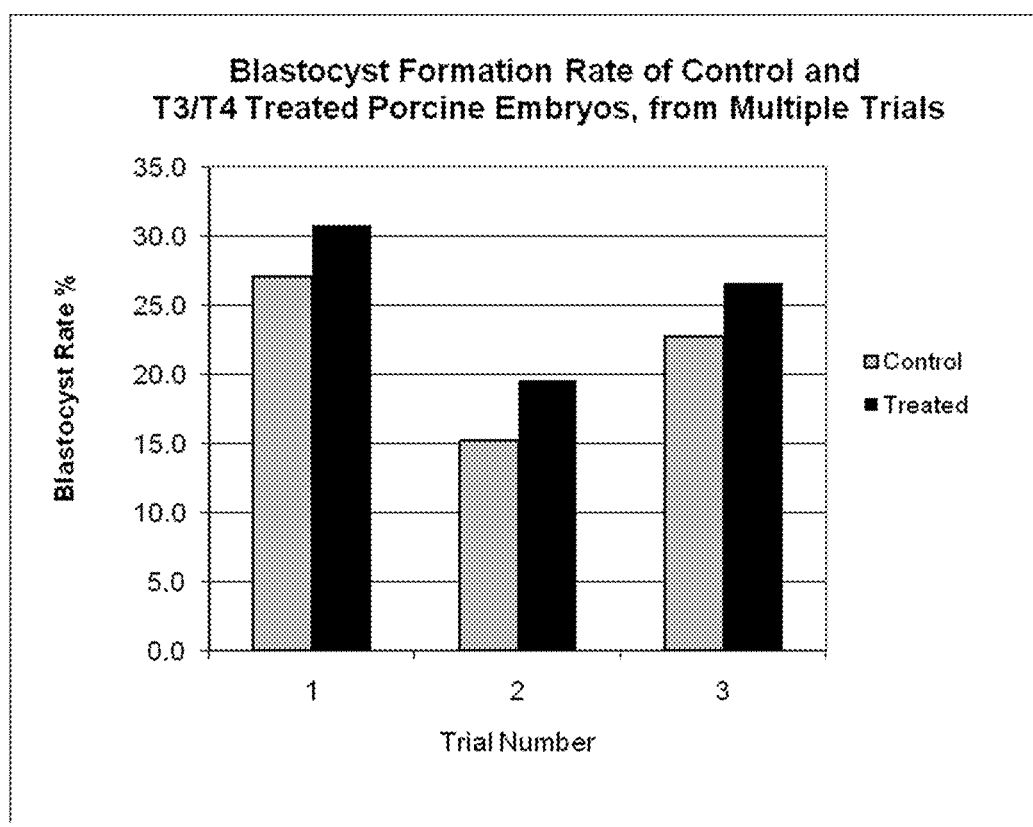
FIG. 15 is a graph showing the blastocyst formation rate in control and T3/T4 treated porcine embryos (n=25 controls, 34 treated), from multiple repeated trials.
Figure 16:
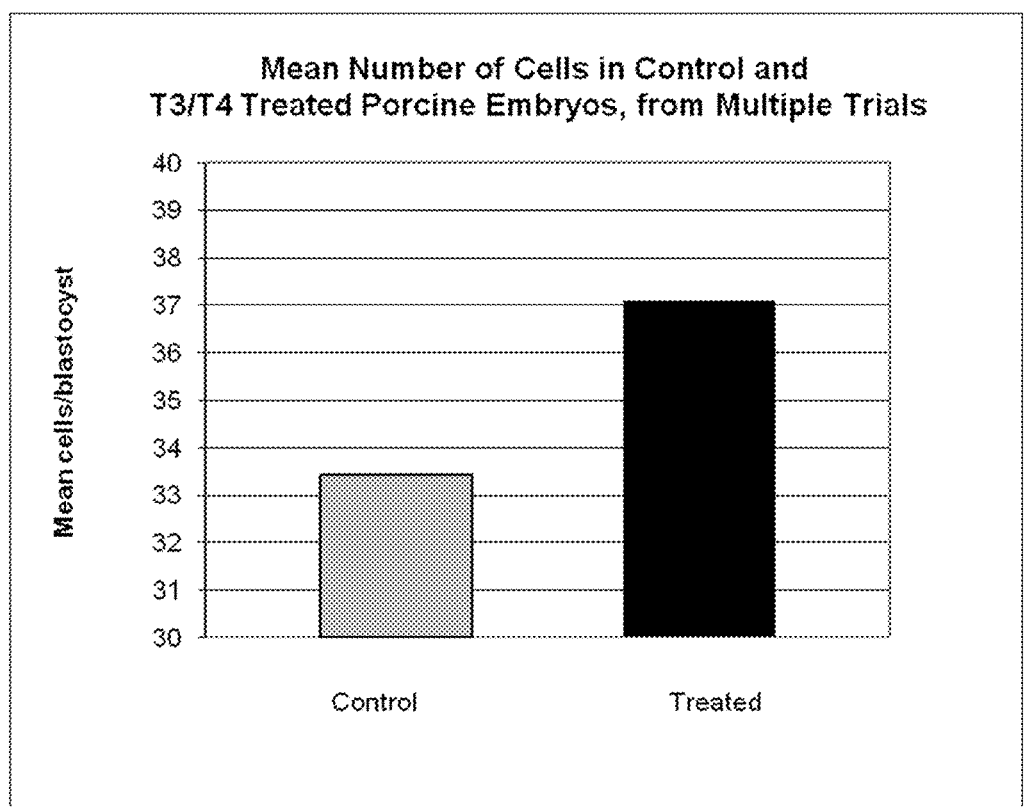
FIG. 16 is a graph showing the mean total number of cells in control and T3/T4 treated porcine embryos (n=25 controls, 34 treated), from multiple repeated trials.

The studies showed that the blastocyst rate was increased in the treated group for each of the three trials compared to controls (FIG. 15). The mean blastocyst rate for all three trials increased from 21.6% in controls to 25.6% in the treated group. The mean number of cells per embryo was increased in the treated group (37.1 cells) relative to controls (33.4 cells) (FIG. 16). The cleavage rate of the treated group was slightly increased relative to controls (FIG. 14).

Discussion

A beneficial effect of embryo culture media containing thyroid hormone (PIVCMT) on porcine in vitro embryo production was identified by numerical increases in blastocyst formation rate and in cell number per blastocyst. Use of culture media containing T3 and T4 for porcine in vitro embryo production improves the blastocyst rates and increases the cell number per blastocyst compared to controls. Therefore embryo culture media containing T3/T4 improves the competency of early embryo development, maturation and survival of porcine embryos.

Example 4

Survival of Frozen-Thawed Embryos Cultured in Different Media

Summary

The effect of culture media containing thyroid hormone on the survival of frozen-thawed bovine embryos was compared to embryos cultured in media not containing thyroid hormone. Improved viability of frozen-thawed bovine embryos was demonstrated in embryos cultured in media containing thyroid hormone as evidenced by improved survival of embryos post-thawing and improved hatching rate of embryos (Table 1).

Methods

Oocyte Maturation, In Vitro Fertilization, and In Vitro Culture

All control and treated bovine oocytes were matured in TCM199 medium with Fetal Bovine Serum (FBS) and additional hormones FSH, LH and E2. Oocytes were fertilized using the method described in Example 2.

The control group of embryos were produced from the one cell stage to the blastocyst stage by culturing them in media. The culture media used was a sequential home-made Synthetic Ovarian Fluid (SOF) based system similar to that used by Tervit et al 1972. The treated group of embryos (SOF+T3+T4) were cultured in SOF similar to the control group except a mixture of T3 and T4 was added to the media to form a concentration of 50 ng/ml.

Cryopreservation and Cryopreservation Media

On Day 7, only the best quality blastocysts (Quality 1) at developmental stages 5, 6, 7 or 8 were selected from both control and treated groups to be used for cryopreservation (blastocyst stage 5=very early, 6=early, 7=expanded, 8=hatching and 9=hatched).

Both treated and control groups were cryopreserved in an ethylene-glycol-sucrose based cryopreservation fluid without the addition of any T3 and T4 using a common regular slow freezing procedure.

Thawing and Evaluating Survival of Thawed Cryopreserved Embryos

All embryos were thawed and then cultured in TCM199 medium with Fetal Bovine Serum (FBS) and pyruvate without any hormones for up to 72 h.

All embryos were evaluated subjectively by a veterinarian trained in the art of embryo evaluation, using light microscopy for viability at several time points post thawing (0, 3, 24, 48 and 72 hours). The results were recorded in Table 1.

Results and Discussion

The results presented in Table 1 demonstrated the positive effect of the addition of T3 and T4 to culture media on the survival rate of bovine embryos post cryopreservation. Embryos cultured in media containing T3 and T4 (SOF+T3+T4) prior to cryopreservation demonstrated a 80%, 60%, and 50% survival rate at 24 hours, 48 hours, and 72 hours post thawing, respectively, compared to 28.6%, 0%, and 0% for the control group, respectively. Likewise, the survival yield of quality 1 or 2 treated embryos was 70%, 60%, and 30% at 24 hours, 48 hours, and 72 hours, respectively, compared to controls, where none of the embryos survived (0% survival). Improved viability and survival of the treated embryos post cryopreservation was also demonstrated by the 30% hatching rate determined at 24 hours, 48 hours, and 72 hours, respectively.

A cryoprotective effect was observed for frozen-thawed embryos treated with culture media containing thyroid hormones prior to cyropreservation. Thus, the results presented in this example confirm those found in Example 2.

While the present disclosure has been described with reference to what are presently considered to be the preferred examples, it is to be understood that the present disclosure is not limited to the disclosed examples. To the contrary, the present disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Survival of Bovine Frozen-Thawed Embryos Cultured in Different Media

| | Culture medium used prior to cryopreservation | | | | | | | |
|---|---|---|---|---|---|---|---|---|
| | SOF (Control Embryos) | | | | SOF + T3 + T4 (Treated Embryos) | | | |
| Total # embryos | 7 | | | | 10 | | | |
| Blastocyst Stage | 5 | 6 | 7 | 8 and 9 | 5 | 6 | 7 | 8 and 9 |
| # Embryos per Stage | 2 | 2 | 2 | 1 | 1 | 2 | 6 | 1 |
| 0 h post thawing | | | | | | | | |
| Viables | 2 | 2 | 2 | 1 | 1 | 2 | 6 | 1 |
| Full size | 2 | 0 | 0 | 0 | 1 | 0 | 0 | 0 |

TABLE 1-continued

Survival of Bovine Frozen-Thawed Embryos Cultured in Different Media

| | Culture medium used prior to cryopreservation | | | | | | | |
|---|---|---|---|---|---|---|---|---|
| | SOF (Control Embryos) | | | | SOF + T3 + T4 (Treated Embryos) | | | |
| Collapsed | 0 | 2 | 2 | 1 | 0 | 2 | 6 | 1 |
| % Viability/Stage | 100.0% | 100.0% | 100.0% | 100.0% | 100.0% | 100.0% | 100.0% | 100.0% |
| % Survival/Total | | | 100.0% | | | | 100.0% | |
| 3 h post thaw | | | | | | | | |
| Viables | 2 | 2 | 2 | 1 | 1 | 2 | 6 | 1 |
| Full size | 2 | 1 | 2 | 0 | 1 | 2 | 2 | 0 |
| Still collapsed | 0 | 1 | 0 | 1 | 0 | 0 | 4 | 1 |
| % Viability/Stage | 100.0% | 100.0% | 100.0% | 100.0% | 100.0% | 100.0% | 100.0% | 100.0% |
| % Survival/Total | | | 100.0% | | | | 100.0% | |
| 24 h post thaw | | | | | | | | |
| Viables | 0 | 0 | 1 | 1 | 1 | 2 | 5 | 0 |
| Quality 1 | 0 | 0 | 0 | 0 | 0 | 1 | 2 | 0 |
| Quality 2 | 0 | 0 | 0 | 0 | 1 | 1 | 2 | 0 |
| Quality 3 | 0 | 0 | 1 | 1 | 0 | 0 | 1 | 0 |
| Hatched embryos | 0 | 0 | 0 | 0 | 0 | 1 | 2 | 0 |
| % Viability/Stage | 0.0% | 0.0% | 50.0% | 100.0% | 100.0% | 100.0% | 83.3% | 0.0% |
| % Survival/Total | | | 28.6% | | | | 80.0% | |
| % Survival Q1/Q2 | | | 0.0% | | | | 70.0% | |
| % Hatching on total | | | 0.0% | | | | 30.0% | |
| 48 h post thaw | | | | | | | | |
| Viables | 0 | 0 | 0 | 0 | 0 | 1 | 5 | 0 |
| Quality 1 | 0 | 0 | 0 | 0 | 0 | 1 | 0 | 0 |
| Quality 2 | 0 | 0 | 0 | 0 | 0 | 0 | 5 | 0 |
| Quality 3 | 0 | 0 | 0 | 0 | 0 | 0 | 0 | 0 |
| Hatched embryos | 0 | 0 | 0 | 0 | 0 | 1 | 2 | 0 |
| % Viability/Stage | 0.0% | 0.0% | 0.0% | 0.0% | 0.0% | 50.0% | 83.3% | 0.0% |
| % Survival/Total | | | 0.0% | | | | 60.0% | |
| % Survival Q1/Q2 | | | 0.0% | | | | 60.0% | |
| % Hatching on total | | | 0.0% | | | | 30.0% | |
| 72 h post thaw | | | | | | | | |
| Viables | 0 | 0 | 0 | 0 | 0 | 1 | 4 | 0 |
| Quality 1 | 0 | 0 | 0 | 0 | 0 | 0 | 1 | 0 |
| Quality 2 | 0 | 0 | 0 | 0 | 0 | 1 | 1 | 0 |
| Quality 3 | 0 | 0 | 0 | 0 | 0 | 0 | 2 | 0 |
| Hatched embryos | 0 | 0 | 0 | 0 | 0 | 1 | 2 | 0 |
| % Viability/Stage | 0.0% | 0.0% | 0.0% | 0.0% | 0.0% | 50.0% | 66.7% | 0.0% |
| % Survival/Total | | | 0.0% | | | | 50.0% | |
| % Survival Q1/Q2 | | | 0.0% | | | | 30.0% | |
| % Hatching on total | | | 0.0% | | | | 30.0% | |

Full Citations For References Referred To In The Specification

1—Sato E and Jiang J Y. 2001. Follicular development and ovulation in hypothyroid rdw rats. Italian Journal of Anatomy and Embryology 106(2 Suppl 2):249-56.

2—Spicer L J, Alonso J, Chamberlain C S. 2001. Effects of thyroid hormones on bovine granulosa and thecal cell function in vitro: Dependence on insulin and gonadotropins. Journal of Dairy Science 84(5):1069-76.

3—Maruo T, Hayashi M, Matsuo H, Yamamoto T, Okada H, Mochizuki M. 1987. The role of thyroid hormone as a biological amplifier of the actions of follicle-stimulating hormone in the functional differentiation of cultured porcine granulosa cells. Endocrinology 121(4):1233-41.

4—Abeydeera L R, Day B N. Fertilization and subsequent development in vitro of pig oocytes inseminated in a modified tris-buffered medium with frozen-thawed ejaculated spermatozoa. Biology of Reproduction, 1997 October; 57(4):729-34.

5—Tervit H R, Whittingham D G, Rowson L E. 1972. Successful culture in vitro of sheep and cattle ova. Journal of Reproduction and Fertility September; 30(3):493-7.

We claim:

1. A method of producing blastocysts in vitro comprising culturing fertilized oocytes in a culture media comprising a thyroid hormone or analog thereof until the blastocysts are produced.

2. The method of claim 1 wherein the thyroid hormone is triiodothyronine (T3).

3. The method of claim 1 wherein the thyroid hormone is thyroxine (T4).

4. The method of claim 1 wherein the thyroid hormone is a combination of triiodothyronine and thyroxine (T3/T4).

5. The method of claim 1 wherein the analog comprises functional fragments of thyroid hormone or peptide mimetics.

6. The method of claim 1 wherein the concentration of hormone or analog is from about 0.1 pmol/L to about 100 ng/ml.

7. The method of claim 1 wherein the concentration of hormone or analog is about 50 ng/ml.

8. The method of claim 1 wherein in vitro blastocyst production comprises a method of maturing blastocysts, the method comprising culturing fertilized oocytes in the culture media until the blastocysts are matured.

9. The method of claim 1 wherein the blastocysts cultured in the culture media exhibit improved survival as compared to blastocysts that were not cultured in the culture media.

10. The method of claim 1 further comprising a method of improving viability of blastocysts post cryopreservation, the method comprising (a) culturing fertilized oocytes in the culture media until blastocysts are produced; and (b) freezing and storing the blastocysts in cryopreservation media to create cryopreserved blastocysts.

11. The method of claim 10 wherein the blastocysts cultured in the culture media exhibit improved viability post cryopreservation as compared to blastocysts that were not cultured in the culture media.

12. The method of claim 1 further comprising the steps of oocyte retrieval, oocyte maturation, and in vitro fertilization prior to culturing the fertilized oocytes.

13. The method of claim 1 further comprising blastocyst transfer or cryopreservation of the blastocysts after culturing the fertilized oocytes.

14. The method of claim 10 wherein the cryopreserved blastocysts are thawed for blastocyst transfer.

15. The method of claim 1 wherein the culturing occurs for a period of 5-8 days.

16. The method of claim 1 wherein the culturing occurs for a period of 5 days.

17. The method of claim 1 for producing a mammalian blastocyst.

18. The method of claim 17 wherein the mammalian blastocyst is bovine, porcine or human.

* * * * *